US010774042B2

(12) United States Patent
Oracz et al.

(10) Patent No.: US 10,774,042 B2
(45) Date of Patent: Sep. 15, 2020

(54) CRYSTALLINE FORMS OF APREMILAST

(71) Applicant: ZAKLADY FARMACEUTYCZNE POLPHARMA SA, Gdanski (PL)

(72) Inventors: Monika Oracz, Kamiensk (PL); Piotr Garczarek, Nysa (PL); Przemyslaw Skoczen, Straszyn (PL); Dominika Podwysocka, Pruszcz Gdanski (PL); Marcin Szulc, Starogard Gdanski (PL); Arkadiusz Majewski, Gdansk (PL)

(73) Assignee: ZAKLADY FARMACEUTYCZNE POLPHARMA SA, Gdanski (PL)

(*) Notice: Subject to any disclaimer, the term of this patent is extended or adjusted under 35 U.S.C. 154(b) by 21 days.

(21) Appl. No.: 16/319,707

(22) PCT Filed: Nov. 21, 2016

(86) PCT No.: PCT/PL2016/000129
§ 371 (c)(1),
(2) Date: Jan. 22, 2019

(87) PCT Pub. No.: WO2017/196192
PCT Pub. Date: Nov. 16, 2017

(65) Prior Publication Data
US 2019/0276400 A1 Sep. 12, 2019

(30) Foreign Application Priority Data
May 12, 2016 (EP) .................... 16169453

(51) Int. Cl.
C07D 209/48 (2006.01)
A61K 9/20 (2006.01)

(52) U.S. Cl.
CPC .............. *C07D 209/48* (2013.01); *A61K 9/20* (2013.01); *C07B 2200/13* (2013.01)

(58) Field of Classification Search
CPC ...... C07D 209/48; C07B 2200/13; A61K 9/20
See application file for complete search history.

(56) References Cited

U.S. PATENT DOCUMENTS

2008/0234359 A1* 9/2008 Muller ................. C07D 209/48
514/417
2017/0298018 A1* 10/2017 Luo ........................ A61P 37/00

FOREIGN PATENT DOCUMENTS

EP 2276483 B1 * 5/2014 ......... A61K 31/4035

* cited by examiner

*Primary Examiner* — Amanda L. Aguirre
(74) *Attorney, Agent, or Firm* — Millen White Zelano and Branigan, PC; Csaba Henter

(57) ABSTRACT

The invention particularly relates to crystalline (solid) forms of N-[2-[(1S)-1-(3-ethoxy-4-methoxyphenyl)-2-(methylsulfonyl)ethyl]-1,3-dioxo-2,3-dihydro-1H-isoindol-4-yl]acetamide), i.e. Form N, Form M, Form O and Form P. It also refers to a pharmaceutical composition or dosage form comprising said crystalline forms. The invention also concerns said pharmaceutical composition or dosage form for use in a method of treating a disease or disorder defined in the claims. Finally, the invention pertains to the use of said novel crystalline forms for the preparation of a pharmaceutical composition or dosage form.

20 Claims, 21 Drawing Sheets

CRYSTALLINE FORMS OF APREMILAST

The invention relates to novel crystalline forms of Apremilast and pharmaceutical compositions/dosage forms containing same. It also refers to processes for preparing said dosage forms and the use thereof for treating patients. Finally, the invention pertains to the use of said novel crystalline forms for the preparation of a pharmaceutical composition or dosage form.

BACKGROUND ART

Apremilast, i.e. N-[2-[(1S)-1-(3-ethoxy-4-methoxyphenyl)-2-(methylsulfonyl)ethyl]-1,3-dioxo-2,3-dihydro-1H-isoindol-4-yl]acetamide), also referred to herein as "APM", has the following chemical formula, wherein "S", if not connected via a chemical bond in the formula, denotes the S-form of the chiral center.

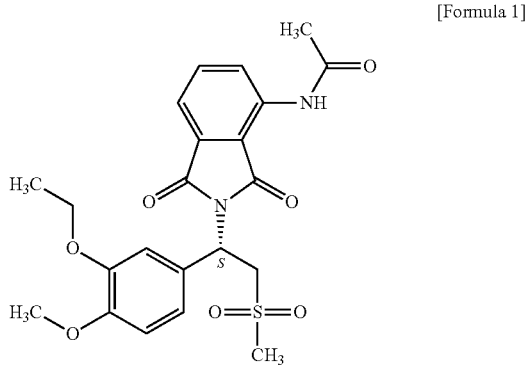

[Formula 1]

Apremilast is a phosphodiesterase 4 inhibitor and blocks the action of an enzyme inside cells called phosphodiesterase 4 (PDE4). This enzyme plays a role in triggering the production of messenger molecules in the immune system called cytokines, which are involved in inflammation and other processes that cause psoriasis and psoriatic arthritis. By blocking PDE4, Apremilast reduces the level of these cytokines in the body, and so reduces the inflammation and other symptoms of psoriasis and psoriatic arthritis. Apremilast is the active ingredient of the medicament Otezla®, distributed by Celgene, Ltd, for the treatment of adults with psoriatic arthritis (inflammation of the joints associated with psoriasis) and moderate to severe plaque psoriasis (a disease causing red, scaly patches on the skin).

EP2276483 B1 discloses various polymorphic forms of Apremilast, i.e. Forms A, B, C, D, E, F and G. Regarding the characterization of these Forms A, B, C, D, E, F and G, in particular their XRPD peak locations and intensity, reference is made to EP2276483 B1. The stability, interconversion and equilibration studies in EP2276483 B1 show that most of these crystalline forms have a high tendency of interconversion, i.e. one polymorphic form converts into another polymorphic form in the presence of solvents.

SUMMARY OF THE INVENTION

The invention particularly relates to crystalline (solid) forms of N-[2-[(1S)-1-(3-ethoxy-4-methoxyphenyl)-2-(methylsulfonyl)ethyl]-1,3-dioxo-2,3-dihydro-1H-isoindol-4-yl]acetamide), i.e. Form N, Form M, Form O and Form P. It also refers to pharmaceutical compositions and dosage forms comprising said crystalline forms. The invention also concerns said pharmaceutical compositions or dosage forms for use in a method of treating a disease or disorder defined in the claims. Finally, the invention pertains to the use of said novel crystalline forms for the preparation of pharmaceutical compositions and dosage forms.

Although Form B is the commercially available form of Apremilast (Otezla®) and has quite good properties, there is a constant need for improvement of existing dosage forms.

Accordingly, one objective underlying the present invention was to improve the existing dosage forms.

DETAILED DESCRIPTION

It has unexpectedly been found that it is possible to provide new valuable polymorphic forms of Apremilast, designated Forms N, M, O and P herein. The crystalline forms described herein may have various benefits over the known crystalline forms.

Figure 7:
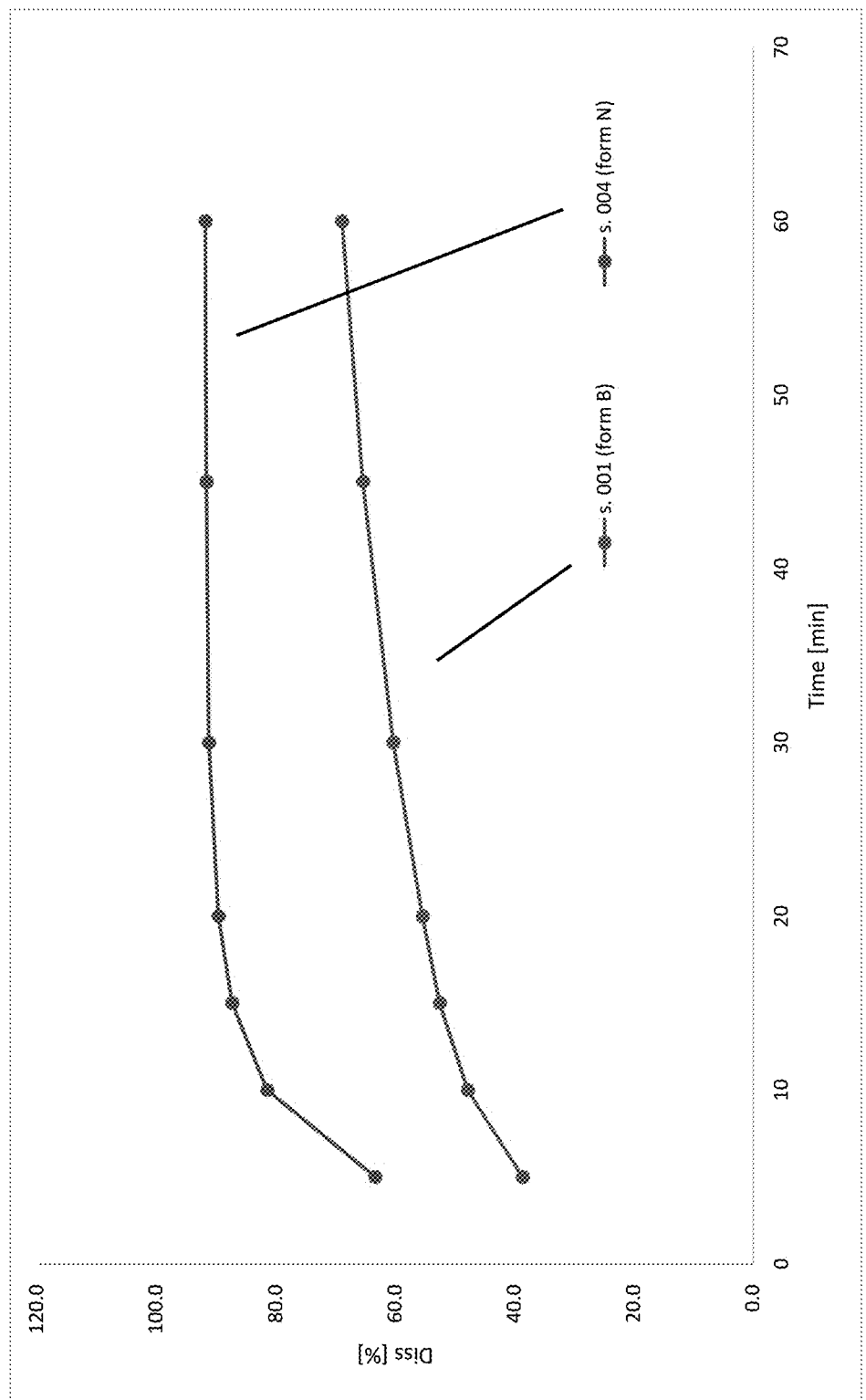
FIG. 7: The figure compares the dissolution profile of Apremilast Form N that of prior art Form B.

In particular, it has been found that tablets comprising Form N show an improved dissolution profile as compared with tablets comprising Form B, wherein Form B is the commercially available form of Apremilast (Otezla®), see Experiment 9 and FIG. 7. That is, when compared with prior art Form B, Form N exhibits a higher dissolution rate by more than 50% at 30 minutes. The comparison with Form B is of greatest interest, since the marketed drug form represents the "gold standard" for any further pharmaceutical development. In addition, it has unexpectedly been found that Form N is a stable crystalline polymorph of Apremilast, which is non-solvated and non-hygroscopic, and has good flow characteristics.

Since EP2276483 B1 already discloses various polymorphic forms of Apremilast, it was not foreseeable, whether further polymorphic forms exist and can be prepared at all. In view of the high interconversion tendency of the known polymorphic forms, it was particularly unexpected that a new, substantially non-hygroscopic and stable (with respect to humidity) polymorph can be prepared (e.g. Form N). It is worth noting that EP2276483 B1 already describes 3 unsolvated or anhydrous crystalline forms, i.e. Forms A, B and F. Therefore, one could not have expected that a further unsolvated, anhydrous form can be prepared, let alone a stable form. Accordingly, there was no reasonable expectation of success that the problems underlying the present invention can indeed be solved by investigating the possible existence of further stable polymorphs. Rather, a skilled person seeking to improve the existing dosage forms would have modified the composition (type and amounts of excipients) of the marketed dosage form or would have improved the structure/type of said final drug dosage forms.

Furthermore, unexpectedly, crystalline Form M of Apremilast has been found, which is also substantially non-hygroscopic. In particular, Form M of Apremilast has superior solubility, particularly compared to prior art Form B. Water solubility of prior art Form B according to literature findings and experimental data is about 7-12 µg/ml, while water solubility of Form M is almost 3 times greater at the same conditions, i.e. is 29 µg/ml. Form B crystallizes as needle-like crystals. Needle-like crystal morphology can cause problems with filterability and flow characteristic. Form M crystallizes as prismatic crystals that have good flow characteristics and filterability and do not form aggregates.

Accordingly, the objective underlying the present invention has been solved.

The invention is further described with respect to the following items:

Items Related to Crystal Form N

N1. Crystalline (solid) form of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (Form N), having an X-ray powder diffraction pattern with peaks at 2-theta angles of 9.9±0.2 degrees 2theta, 12.7±0.2 degrees 2theta, 18.8±0.2 degrees 2theta, 20.2±0.2 degrees 2theta, 22.1±0.2 degrees 2theta, 24.0±0.2 degrees 2theta, and 29.4±0.2 degrees 2theta when using Cu-Kα radiation.

N2. The crystalline form of item N1, having a single endothermic event in a differential scanning calorimeter (DSC) plot. The applied temperature range is 25-250° C.

N3. The crystalline form of item N1 or N2, having an endothermic event in a differential scanning calorimeter plot with an onset temperature of about 139° C.±6° C., about 139° C.±4° C., or about 139° C.±2° C.

N4. The crystalline form of any of items N1-3, having an X-ray powder diffraction pattern, wherein the peak at 22.1±0.2 degrees 2theta has the highest intensity (set to 100).

N5. The crystalline form of any of items N1-4, wherein the X-ray powder diffraction pattern is free of further peaks having an intensity which is higher than the intensity of the peak at 18.8±0.2 degrees 2theta.

N6. The crystalline form of any of items N1-5, wherein the X-ray powder diffraction pattern has further peaks at 2-theta angles of 11.7±0.2 degrees 2theta, 11.9±0.2 degrees 2theta, 13.7±0.2 degrees 2theta, 14.4±0.2 degrees 2theta, 14.6±0.2 degrees 2theta, 15.3±0.2 degrees 2theta, 16.7±0.2 degrees 2theta, 21.4±0.2 degrees 2theta, 23.0±0.2 degrees 2theta, 23.7±0.2 degrees 2theta, 24.8±0.2 degrees 2theta, 25.6±0.2 degrees 2theta, 26.8±0.2 degrees 2theta, and 29.8±0.2 degrees 2theta, when using Cu-Kα radiation.

N7. The crystalline form of any of items N1-6, wherein said X-ray powder diffraction pattern is free of further peaks which have an intensity which is in the range of intensities of the peaks defined in items N1 and N6, in particular the X-ray powder diffraction pattern is free of further peaks having an intensity which is higher than the intensity of the peak at 29.8±0.2 degrees 2theta.

N8. The crystalline form of any of items N1-7, which is substantially polymorphically pure, i.e. contains less than 5 wt.-%, or less than 1 wt.-% of other crystalline, non-crystalline or amorphous forms of N-[2-[(1S)-1-(3-ethoxy-4-methoxyphenyl)-2-(methylsulfonyl)ethyl]-1,3-dioxo-2,3-dihydro-1H-isoindol-4-yl]acetamide.

N9. The crystalline form of any of items N1-8, which is substantially pure, i.e. contains less than 1 area-%, or less than 0.5 area-%, preferably less than 0.1 area-%, of compounds other than N-[2-[(1S)-1-(3-ethoxy-4-methoxyphenyl)-2-(methylsulfonyl)ethyl]-1,3-dioxo-2,3-dihydro-1H-isoindol-4-yl]acetamide) as determined by quantitative $^{13}$C NMR measurement or high performance liquid chromatography (HPLC).

N10. The crystalline form of any of items N1-9, which is unsolvated, preferably has a solvent content of less than 1 wt.-%, or less than 0.5 wt.-%, preferably less than 0.2 wt.-%, or even less than 0.15 wt.-%, wherein the solvent content is determined by gas chromatographic (GC) analysis and the water content is determined by the method according to Karl Fischer. Form N is free of any solvent including water.

N11. The crystalline form of any of items N1-10, having a mass loss of less than 0.5% of the total mass of the sample in a thermogravimetric analysis (TGA) upon heating from 25° C. to 250° C. with the gradient of 7° C./min.

N13. The crystalline form of any of items N1-12, having an X-ray powder diffraction pattern with peaks and/or intensities as shown in Table 5 (below) or FIG. 3.

N14. The crystalline form of any of items N1-13, wherein the peaks recited in item N1 and/or item N6 have intensities as shown in the following Table 1:

| 2-theta(deg) | Rel. int. I(a.u.) | Preferred intensities Rel. int. I(a.u.) |
|---|---|---|
| 9.9 | 7-20 | 12.95 |
| 10.34 | 2-13 | 6.93 |
| 10.8 | 1-8 | 1.53 |
| 11.7 | 20-35 | 26.45 |
| 11.9 | 9-20 | 13.80 |
| 12.7 | 20-32 | 25.49 |
| 13.7 | 20-32 | 25.29 |
| 14.4 | 11-21 | 15.85 |
| 14.6 | 8-20 | 14.71 |
| 15.3 | 10-22 | 16.73 |
| 16.1 | 1-7 | 1.93 |
| 16.7 | 15-27 | 20.64 |
| 16.9 | 2-12 | 6.38 |
| 18.1 | 2-12 | 6.84 |
| 18.8 | 25-40 | 31.17 |
| 20.2 | 20-38 | 27.84 |
| 20.6 | 2-12 | 6.89 |
| 21.4 | 5-16 | 10.52 |
| 22.1 | 100 | 100.00 |
| 23.0 | 10-22 | 15.78 |
| 23.7 | 9-21 | 14.79 |
| 24.0 | 30-55 | 43.66 |
| 24.8 | 8-20 | 14.19 |
| 25.6 | 17-36 | 25.33 |
| 26.2 | 1-10 | 5.25 |
| 26.8 | 10-23 | 17.14 |
| 28.1 | 4-16 | 9.92 |
| 29.4 | 10-28 | 17.25 |
| 29.8 | 4-17 | 10.04 |
| 31.4 | 1-14 | 6.44 |
| 32.3 | 1-12 | 7.26 |

Items Related to Form M

M1. Crystalline (solid) form of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (Form M), containing 0.3-0.7 moles of ethyl acetate per of mole N-[2-[(1S)-1-(3-ethoxy-4-methoxyphenyl)-2-(methylsulfonyl)ethyl]-1,3-dioxo-2,3-dihydro-1H-isoindol-4-yl]acetamide), having an X-ray powder diffraction pattern with peaks at 2-theta angles of 7.5±0.2 degrees 2theta, 9.1±0.2 degrees 2theta, 11.3±0.2 degrees 2theta, 12.0±0.2 degrees 2theta, 16.4±0.2 degrees 2theta, 17.7±0.2 degrees 2theta, 19.3±0.2 degrees 2theta, 21.4±0.2 degrees 2theta, 22.5±0.2 degrees 2theta, 24.7±0.2 degrees 2theta, 25.4±0.2 degrees 2theta, 26.3±0.2 degrees 2theta, 27.5±0.2 degrees 2theta, and 34.3±0.2 degrees 2theta, when using Cu-Kα radiation.

The solvent molecules, i.e. ethyl acetate, are contained in the crystal lattice.

M2. The crystalline form of item M1, having a single endothermic event in a differential scanning calorimeter (DSC) plot. The applied temperature range is 25-250° C.

M3. The crystalline form of item M1 or M2, having an endothermic event in a differential scanning calorimeter plot with an onset temperature of about 103° C.±6° C., about 103° C.±4° C., or about 103° C.±2° C.

M4. The crystalline form of any of items M1-3, having an X-ray powder diffraction pattern, wherein the peaks at 2-theta angles of 7.5±0.2 degrees 2theta, 11.3±0.2 degrees 2theta, 16.4±0.2 degrees 2theta, 17.7±0.2 degrees 2theta, 19.3±0.2 degrees 2theta, 21.4±0.2 degrees 2theta, 22.5±0.2 degrees 2theta, 24.7±0.2 degrees 2theta, 25.4±0.2 degrees 2theta, 26.3±0.2 degrees 2theta, and 27.5±0.2 degrees 2theta represent the peaks with highest intensity, and/or wherein the peak at 26.3±0.2 degrees 2theta has the highest intensity (set to 100).

M5. The crystalline form of any of items M1-4, wherein said X-ray powder diffraction pattern is free of further peaks which have an intensity which is in the range of the intensities of the peaks defined in item M4, in particular the X-ray powder diffraction pattern is free of further peaks having an intensity which is higher than the intensity of the peak at 27.5±0.2 degrees 2theta.

M6. The crystalline form of any of items M1-5, wherein the X-ray powder diffraction pattern has further peaks at 2-theta angles of 14.0±0.2 degrees 2theta, 15.2±0.2 degrees 2theta, 15.3±0.2 degrees 2theta, 20.2±0.2 degrees 2theta, 20.7±0.2 degrees 2theta, 22.8±0.2 degrees 2theta, 23.2±0.2 degrees 2theta, 23.4±0.2 degrees 2theta, and 29.0±0.2 degrees 2theta, when using Cu-Kα radiation.

M7. The crystalline form of any of items M1-6, wherein said X-ray powder diffraction pattern is free of further peaks which have an intensity which is in the range of the intensities of the peaks defined in items M1 and M6, in particular the X-ray powder diffraction pattern is free of further peaks having an intensity which is higher than the intensity of the peak at 22.8 degrees 2theta.

M8. The crystalline form of any of items M1-7, which is substantially polymorphically pure, i.e. contains less than 5 wt.-%, or less than 1 wt.-% of other crystalline, non-crystalline or amorphous forms of N-[2-[(1S)-1-(3-ethoxy-4-methoxyphenyl)-2-(methylsulfonyl)ethyl]-1,3-dioxo-2,3-dihydro-1H-isoindol-4-yl]acetamide.

M9. The crystalline form of any of items M1-8, which is substantially pure, i.e. contains less than 1 area-%, or less than 0.5 area-%, preferably less than 0.1 area-%, of compounds other than N-[2-[(1S)-1-(3-ethoxy-4-methoxyphenyl)-2-(methylsulfonyl)ethyl]-1,3-dioxo-2,3-dihydro-1H-isoindol-4-yl]acetamide) as determined by quantitative $^{13}$C NMR measurement or high performance liquid chromatography (HPLC).

M10. The crystalline form of any of items M1-9, which is an ethyl acetate solvate, preferably containing 0.4-0.6 moles of ethyl acetate per mole of N-[2-[(1S)-1-(3-ethoxy-4-methoxyphenyl)-2-(methylsulfonyl)ethyl]-1,3-dioxo-2,3-dihydro-1H-isoindol-4-yl]acetamide), preferably it is a hemi-ethyl acetate solvate, i.e. N-[2-[(1S)-1-(3-ethoxy-4-methoxyphenyl)-2-(methylsulfonyl)ethyl]-1,3-dioxo-2,3-dihydro-1H-isoindol-4-yl]acetamide).$0.5C_4H_8O_2$.

M11. The crystalline form of any of items M1-10, having a mass loss of more than 8%, e.g. about 8.5%, of the total mass of the sample, corresponding to a loss of ethyl acetate, in a thermogravimetric analysis (TGA) upon heating from 25° C. to 220° C. with the gradient of 7° C./min.

M12. The crystalline form of any of items M1-11, having a mass change of less than 0.8%, less than 0.5%, or less than 0.2% of the total mass of the sample in a moisture sorption analysis from close to 0% relative humidity to 90% relative humidity.

M14. The crystalline form of any of items M1-13, having an X-ray powder diffraction pattern with peaks and/or intensities as shown in Table 6 (below) or FIG. 10.

M15. The crystalline form of any of items M1-14, wherein the peaks recited in item M1 and/or item M6 have intensities as shown in the following Table 2:

| 2-theta(deg) | Rel. Int. I(a.u.) | Preferred intensities Rel. Int. I(a.u.) |
|---|---|---|
| 7.5 | 50-75 | 64.05 |
| 9.1 | 8-22 | 14.28 |
| 9.7 | 1-12 | 5.10 |
| 11.3 | 30-55 | 46.19 |

-continued

| 2-theta(deg) | Rel. Int. I(a.u.) | Preferred intensities Rel. Int. I(a.u.) |
|---|---|---|
| 12.0 | 8-20 | 12.88 |
| 14.0 | 10-27 | 18.37 |
| 15.2 | 10-22 | 15.09 |
| 15.3 | 5-16 | 10.72 |
| 16.4 | 30-55 | 45.72 |
| 17.7 | 55-90 | 70.79 |
| 19.3 | 25-40 | 32.37 |
| 20.2 | 14-28 | 19.62 |
| 20.7 | 8-22 | 14.84 |
| 21.4 | 25-45 | 34.11 |
| 22.5 | 24-43 | 32.68 |
| 22.8 | 5-16 | 10.32 |
| 23.2 | 10-22 | 15.25 |
| 23.4 | 15-32 | 22.12 |
| 24.7 | 25-45 | 34.29 |
| 25.4 | 23-43 | 32.30 |
| 26.3 | 100 | 100.00 |
| 27.5 | 23-40 | 30.53 |
| 29.0 | 15-30 | 20.37 |
| 29.7 | 2-14 | 7.97 |
| 30.5 | 1-12 | 4.70 |
| 34.3 | 8-20 | 14.62 |

Items Related to Form O

O1. Crystalline (solid) form of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (Form 0), containing 0.3-0.7 moles of dimethylacetamide per mole of N-[2-[(1S)-1-(3-ethoxy-4-methoxyphenyl)-2-(methylsulfonyl)ethyl]-1,3-dioxo-2,3-dihydro-1H-isoindol-4-yl]acetamide) and
having an X-ray powder diffraction pattern with peaks at 2-theta angles of 7.5±0.2 degrees 2theta, 11.2±0.2 degrees 2theta, 15.3±0.2 degrees 2theta, 16.4±0.2 degrees 2theta, 17.7±0.2 degrees 2theta, 21.4±0.2 degrees 2theta, 22.5±0.2 degrees 2theta, 23.5±0.2 degrees 2theta, 24.8±0.2 degrees 2theta, 25.5±0.2 degrees 2theta, 26.4±0.2 degrees 2theta, and 27.5±0.2 degrees 2theta, when using Cu-Kα radiation.

The solvent molecules, i.e. dimethylacetamide, are contained in the crystal lattice.

O2. The crystalline form of item O1, having a single endothermic event in a differential scanning calorimeter (DSC) plot. The applied temperature range is 25-250° C.

O3. The crystalline form of item O1 or O2, having an endothermic event in a differential scanning calorimeter plot with an onset temperature of about 124° C.±6° C., about 124° C.±4° C., or about 124° C.±2° C.

O4. The crystalline form of any of items O1-3, having an X-ray powder diffraction pattern, wherein the peaks recited in item O1 represent the peaks with highest intensity, and/or wherein the peak at 26.4±0.2 degrees 2theta has the highest intensity (set to 100).

O5. The crystalline form of any of items O1-4, wherein said X-ray powder diffraction pattern is free of further peaks which have an intensity which is in the range of the intensities of the peaks defined in item O1, in particular the X-ray powder diffraction pattern is free of further peaks having an intensity which is higher than the intensity of the peak at 21.4±0.2 degrees 2theta.

O6. The crystalline form of any of items O1-5, wherein the X-ray powder diffraction pattern has further peaks at 2-theta angles of 9.1±0.2 degrees 2theta, 11.9±0.2 degrees 2theta, 13.8±0.2 degrees 2theta, 14.0±0.2 degrees 2theta, 19.4±0.2 degrees 2theta, 20.3±0.2 degrees 2theta, and 29.8±0.2 degrees 2theta, when using Cu-Kα radiation.

O7. The crystalline form of any of items O1-6, wherein said X-ray powder diffraction pattern is free of further peaks which have an intensity which is in the range of the intensities of the peaks defined in items O1 and O6, in particular the X-ray powder diffraction pattern is free of further peaks having an intensity which is higher than the intensity of the peak at 14.0±0.2 degrees 2theta.

O8. The crystalline form of any of items O1-7, which is substantially polymorphically pure, i.e. contains less than 5 wt.-% or less than 1 wt.-% of other crystalline, non-crystalline, or amorphous forms of N-[2-[(1S)-1-(3-ethoxy-4-methoxyphenyl)-2-(methylsulfonyl)ethyl]-1,3-dioxo-2,3-dihydro-1H-isoindol-4-yl]acetamide.

O9. The crystalline form of any of items O1-8, which is substantially pure, i.e. contains less than 1 area-%, or less than 0.5 area-%, preferably less than 0.1 area-%, of compounds other than N-[2-[(1S)-1-(3-ethoxy-4-methoxyphenyl)-2-(methylsulfonyl)ethyl]-1,3-dioxo-2,3-dihydro-1H-isoindol-4-yl]acetamide) and dimethylacetamide as determined by quantitative $^{13}$C NMR measurement or high performance liquid chromatography (HPLC).

O10. The crystalline form of any of items O1-9, which is a dimethylacetamide (DMA) solvate, preferably containing 0.4-0.6 moles of dimethylacetamide per mole of N-[2-[(1S)-1-(3-ethoxy-4-methoxyphenyl)-2-(methylsulfonyl)ethyl]-1,3-dioxo-2,3-dihydro-1H-isoindol-4-yl]acetamide), further preferred comprising about 0.5 of molar equivalents of DMA, e.g. the crystalline form is N-[2-[(1S)-1-(3-ethoxy-4-methoxyphenyl)-2-(methylsulfonyl)ethyl]-1,3-dioxo-2,3-dihydro-1H-isoindol-4-yl]acetamide).0.5$C_4H_9NO$.

O11. The crystalline form of any of items O1-10, having a mass loss of more than 7%, e.g. about 7.8%, which corresponds to the loss of dimethylacetamide as confirmed by gas chromatographic analysis, of the total mass of the sample in a thermogravimetric analysis (TGA) upon heating from 25° C. to 220° C. with the gradient of 7° C./min.

O12. The crystalline form of any of items O1-11, which does not contain any amorphous form of N-[2-[(1S)-1-(3-ethoxy-4-methoxyphenyl)-2-(methylsulfonyl)ethyl]-1,3-dioxo-2,3-dihydro-1H-isoindol-4-yl]acetamide).

O13. The crystalline form of any of items O1-12, wherein the peaks recited in item O1 and/or item O6 have intensities as shown in the following Table 3:

| 2-theta(deg) | Rel. int. I(a.u.) | Preferred intensities Rel. int. I(a.u.) |
|---|---|---|
| 7.5 | 40-70 | 56.54 |
| 9.1 | 4-18 | 11.02 |
| 9.7 | 2-16 | 9.57 |
| 10.1 | 1-9 | 3.10 |
| 11.2 | 30-60 | 45.57 |
| 11.9 | 5-22 | 12.37 |
| 13.2 | 1-12 | 5.17 |
| 13.8 | 5-22 | 11.97 |
| 14.0 | 5-22 | 10.67 |
| 15.3 | 25-50 | 35.90 |
| 16.4 | 35-60 | 44.85 |
| 17.7 | 70-95 | 87.42 |
| 19.2 | 2-16 | 9.21 |
| 19.4 | 15-28 | 20.61 |
| 20.3 | 10-23 | 16.88 |
| 20.8 | 1-12 | 5.83 |
| 21.4 | 15-35 | 24.81 |
| 22.5 | 22-45 | 33.63 |
| 22.8 | 2-16 | 8.80 |

-continued

| 2-theta(deg) | Rel. int. I(a.u.) | Preferred intensities Rel. int. I(a.u.) |
|---|---|---|
| 23.5 | 22-40 | 29.97 |
| 23.9 | 1-9 | 3.30 |
| 24.8 | 27-50 | 38.26 |
| 25.5 | 20-37 | 25.94 |
| 26.4 | 100 | 100.00 |
| 27.5 | 25-50 | 34.55 |
| 28.5 | 1-12 | 5.62 |
| 29.0 | 15-30 | 21.83 |
| 29.8 | 2-16 | 9.96 |

O14. The crystalline form of any of items O1-13, having an X-ray powder diffraction pattern with peaks and/or intensities as shown in Table 12 or FIG. 15.

Items Related to Form P

P1. Crystalline (solid) form of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (Form P), containing 0.1-1.0 moles of dimethylformamide per mole of N-[2-[(1S)-1-(3-ethoxy-4-methoxyphenyl)-2-(methylsulfonyl)ethyl]-1,3-dioxo-2,3-dihydro-1H-isoindol-4-yl]acetamide) and
having an X-ray powder diffraction pattern with peaks at 2-theta angles of 7.4±0.2 degrees 2theta, 11.2±0.2 degrees 2theta, 15.3±0.2 degrees 2theta, 16.3±0.2 degrees 2theta, 17.7±0.2 degrees 2theta, 19.3±0.2 degrees 2theta, 20.3±0.2 degrees 2theta, 21.3±0.2 degrees 2theta, 22.5±0.2 degrees 2theta, 23.5±0.2 degrees 2theta, 24.7±0.2 degrees 2theta, 25.5±0.2 degrees 2theta, 26.3±0.2 degrees 2theta, 27.3±0.2 degrees 2theta, 27.5±0.2 degrees 2theta, and 28.9±0.2 degrees 2theta, when using Cu-Kα radiation.

The solvent molecules, i.e. dimethylformamide, are contained in the crystal lattice.

P2. The crystalline form of item P1, having a single endothermic event in a differential scanning calorimeter (DSC) plot. The applied temperature range is 25-250° C.

P3. The crystalline form of item P1 or P2, having an endothermic event in a differential scanning calorimeter plot with an onset temperature of about 94° C.±6° C., about 94° C.±4° C., or about 94° C.±2° C.

P4. The crystalline form of any of items P1-3, having an X-ray powder diffraction pattern, wherein the peaks recited in item P1 represent the peaks with highest intensity, and/or wherein the peak at 26.3±0.2 degrees 2theta has the highest intensity (set to 100).

P5. The crystalline form of any of items P1-4, wherein said X-ray powder diffraction pattern is free of further peaks which have an intensity which is in the range of the intensities of the peaks defined in item P1, in particular the X-ray powder diffraction pattern is free of further peaks having an intensity which is higher than the intensity of the peak at 15.3±0.2 degrees 2theta.

P6. The crystalline form of any of items P1-5, wherein the X-ray powder diffraction pattern has further peaks at 2-theta angles of 9.0±0.2 degrees 2theta, 11.8±0.2 degrees 2theta, 14.0±0.2 degrees 2theta, 19.0±0.2 degrees 2theta, 20.8±0.2 degrees 2theta, and 23.7±0.2 degrees 2theta, when using Cu-Kα radiation.

P7. The crystalline form of any of items P1-6, wherein said X-ray powder diffraction pattern is free of further peaks which have an intensity which is in the range of the intensities of the peaks defined in items P1 and P6, in particular the X-ray powder diffraction pattern is free of further peaks having an intensity which is higher than the intensity of the peak at 19.0±0.2 degrees 2theta.

P8. The crystalline form of any of items P1-7, which is substantially polymorphically pure, i.e. contains less than 5 wt.-% or less than 1 wt.-% of other crystalline, non-crystalline or amorphous forms of N-[2-[(1S)-1-(3-ethoxy-4-methoxyphenyl)-2-(methylsulfonyl)ethyl]-1,3-dioxo-2,3-dihydro-1H-isoindol-4-yl]acetamide.

P9. The crystalline form of any of items P1-8, which is substantially pure, i.e. contains less than 1 area-%, or less than 0.5 area-%, preferably less than or 0.1 area-%, of compounds other than N-[2-[(1S)-1-(3-ethoxy-4-methoxyphenyl)-2-(methylsulfonyl)ethyl]-1,3-dioxo-2,3-dihydro-1H-isoindol-4-yl]acetamide) and dimethylformamide as determined by quantitative $^{13}$C NMR measurement or high performance liquid chromatography (HPLC).

P10. The crystalline form of any of items P1-9, which is a dimethylformamide (DMF) solvate, which preferably comprises 0.7 or less; further preferred 0.4-0.6 moles of DMF per mole of N-[2-[(1S)-1-(3-ethoxy-4-methoxyphenyl)-2-(methylsulfonyl)ethyl]-1,3-dioxo-2,3-dihydro-1H-isoindol-4-yl]acetamide), e.g. the crystalline form is N-[2-[(1S)-1-(3-ethoxy-4-methoxyphenyl)-2-(methylsulfonyl)ethyl]-1,3-dioxo-2,3-dihydro-1H-isoindol-4-yl]acetamide).0.5C$_3$H$_7$NO.

P11. The crystalline form of any of items P1-10, having a mass loss of more than 7%, e.g. about 7.4%, which corresponds to the loss of dimethylformamide as confirmed by gas chromatographic analysis, of the total mass of the sample in a thermogravimetric analysis (TGA) upon heating from 25° C. to 220° C. with the gradient of 7° C./min.

P12. The crystalline form of any of items P1-11, which does not contain any amorphous form of N-[2-[(1S)-1-(3-ethoxy-4-methoxyphenyl)-2-(methylsulfonyl)ethyl]-1,3-dioxo-2,3-dihydro-1H-isoindol-4-yl]acetamide).

P13. The crystalline form of any of items P1-12, having an X-ray powder diffraction pattern with peaks and/or intensities as shown in Table 13 or FIG. 19.

P14. The crystalline form of any of items P1-13, wherein the peaks recited in item P1 and/or item P6 have intensities as shown in the following Table 4:

| 2-theta(deg) | Rel. int. I(a.u.) | Preferred intensities Rel. int. I(a.u.) |
|---|---|---|
| 7.4 | 40-70 | 54.31 |
| 9.0 | 5-22 | 13.80 |
| 9.7 | 1-14 | 4.28 |
| 11.2 | 40-70 | 51.06 |
| 11.8 | 5-22 | 14.59 |
| 13.1 | 2-12 | 6.81 |
| 13.7 | 2-12 | 8.46 |
| 14.0 | 10-28 | 19.62 |
| 15.3 | 20-40 | 31.07 |
| 16.3 | 20-50 | 39.11 |
| 17.7 | 65-95 | 83.78 |
| 18.1 | 1-14 | 4.14 |
| 19.0 | 5-20 | 10.30 |
| 19.3 | 18-40 | 28.62 |
| 20.3 | 15-32 | 21.45 |
| 20.8 | 5-22 | 10.15 |
| 21.3 | 25-50 | 38.78 |
| 22.5 | 25-50 | 37.15 |
| 22.7 | 2-16 | 8.84 |
| 22.9 | 2-12 | 4.65 |
| 23.5 | 25-50 | 41.81 |
| 23.7 | 6-22 | 12.41 |
| 24.7 | 25-50 | 41.49 |

-continued

| 2-theta(deg) | Rel. int. I(a.u.) | Preferred intensities Rel. int. I(a.u.) |
|---|---|---|
| 25.5 | 20-40 | 31.97 |
| 26.3 | 100 | 100.00 |
| 27.3 | 15-35 | 22.14 |
| 27.5 | 15-35 | 21.75 |
| 28.9 | 15-35 | 23.03 |

Items Related to all Crystalline Forms N, M, O and P
1. Pharmaceutical composition or dosage form comprising a crystalline form of any of items N1-N14, M1-M15, O1-O14 and P1-P14, preferably any of items N1-N14 and M1-M15, most preferably any of items N1-N14, or a mixture of any of the aforementioned crystalline forms.
2. The pharmaceutical dosage form of item 1, wherein the pharmaceutical dosage form is a solid oral dosage form, preferably a tablet.
3. The pharmaceutical composition or dosage form of item 1 or 2, which comprises at least one pharmaceutically acceptable excipient.
4. Pharmaceutical composition or dosage form of any of items 1-3, particularly preferred dosage forms/compositions with Form N or Form M, most preferably with Form N, for use in a method of treating a disease or disorder selected from the group consisting of: psoriasis; psoriatic arthritis; rheumatoid arthritis; chronic cutaneous sarcoid; giant cell arteritis; Parkinson's Disease; prurigo nodularis; lichen planus; complex apthosis; Behcet's Disease; lupus; hepatitis; uveitis; Sjogren's Disease; depression; interstitial cystitis; vulvodynia; prostatitis; osteoarthritis; diffuse large B cell lymphoma; polymysoitis; dermatomyositis; inclusion body myositis; erosive osteoarthritis; interstitial cystitis; hepatitis; endometriosis; radiculopathy; and pyoderma gangrenosum.
5. Pharmaceutical composition or dosage form of any of items 1-3, particularly preferred dosage forms/compositions with Form N or Form M, most preferably with Form N, for use in a method of treating or preventing a disease or disorder selected from the group consisting of: HIV; hepatitis; adult respiratory distress syndrome; bone resorption diseases; chronic obstructive pulmonary diseases; chronic pulmonary inflammatory diseases; dermatitis; inflammatory skin disease, atopic dermatitis, cystic fibrosis; septic shock; sepsis; endotoxic shock; hemodynamic shock; sepsis syndrome; post ischemic re perfusion injury; meningitis; psoriasis; psoriatic arthritis; fibrotic disease; cachexia; graft rejection including graft versus host disease; auto immune disease; rheumatoid spondylitis; arthritic conditions, such as rheumatoid arthritis and osteoarthritis; osteoporosis; Crohn's disease; ulcerative colitis; inflammatory bowel disease; multiple sclerosis; systemic lupus erythrematosus; erythema nodosum leprosum in leprosy; radiation damage; asthma; and hyperoxic alveolar injury. Preferably, the pharmaceutical compositions or dosage forms described herein are used for treating psoriatic arthritis or plaque psoriasis.
6. Use of a crystalline form of any of items N1-N14, M1-M15, O1-O14 and P1-P14 or a mixture of said crystalline forms for the preparation of a pharmaceutical composition or dosage form.
7. The use of item 6, wherein the crystalline form is Form N, which is used as the starting material for preparing an oral solid pharmaceutical dosage form comprising Form N.
8. Process for preparing an oral solid pharmaceutical dosage form of any of items 1-3, comprising a step of compressing (i) a mixture of Form N with one or more pharmaceutical acceptable excipients (e.g. by applying direct compression techniques), or (ii) granules including Form N, optionally in admixture with one or more excipients, in order to provide a tablet. The granules can e.g. be prepared by dry granulation such as (roller) compaction, or slugging.

By way of example, the dosage form can be prepared by using a process comprising or consisting of the following steps:
(i) Pass Apremilast, e.g. Form N, and one or more pharmaceutically acceptable excipients, preferably one or more (further preferred all) of lactose monohydrate, microcrystalline cellulose, and croscarmellose sodium through a sieve, e.g. a 0.425 mm sieve;
(ii) Mix the ingredients from step (i), e.g. in a blender, e.g. for 15 min at 25 RPM;
(iii) Optionally, add a lubricant, e.g. magnesium stearate, and mix for e.g. 5 min at 12 RPM; and
(iv) Compress the blend of step (iii) using e.g. a single punch machine equipped with oval punch (14×8 mm), e.g. at a compression force of 7 kN, in order to prepare a tablet.

9. Process for preparing an oral solid pharmaceutical dosage form comprising an amorphous form of N-[2-[(1S)-1-(3-ethoxy-4-methoxyphenyl)-2-(methylsulfonyl)ethyl]-1,3-dioxo-2,3-dihydro-1H-isoindol-4-yl]acetamide), wherein the process comprises a step of dissolving a crystalline form of APM as described herein, preferably Form M, and optionally one or more pharmaceutically acceptable excipients, in a solvent or mixture of solvents, preferably in acetone, and (i) spraying the resulting solution onto pharmaceutical acceptable excipients, e.g. particles, granules, or a tablet core, or (ii) spray drying the resulting solution, while performing a drying step during and/or after the spraying step. The spraying and drying process provides an amorphous form of Apremilast.

By way of example, the dosage form can be prepared by using a process comprising or consisting of the following steps:
i) Dissolve Apremilast (Form M) in a solvent, preferably acetone;
ii) Pass one or more pharmaceutically acceptable excipient(s), preferably one or more (further preferred all) of lactose monohydrate, microcrystalline cellulose, croscarmellose sodium through a sieve, e.g. a 0.425 mm sieve;
iii) Place the ingredients from step (ii) in a fluid bed granulator (e.g. equipped with top spray nozzle) and granulate it by spraying the solution from step (i); iv) Dry the obtained granulate;
v) Add a lubricant, e.g. magnesium stearate, and mix for e.g. 5 min at 12 RPM; and
vi) Optionally compress the blend from step (v), e.g. by using a single punch machine equipped with oval punch (14×8 mm) at a compression force of 7 kN, in order to prepare a tablet. The blend of step (v) can also be used as is, e.g. can be filled in sachets.

10. Use of a crystalline form of any of items N1-N14, M1-M15, O1-O14 and P1-P14, preferably the crystalline Form N of items N1-N14, as a starting material for preparing an oral solid pharmaceutical dosage form comprising said crystalline form or a different crystalline or an amorphous form.

11. Method of treating a patient by administering an effective amount of any of the crystalline Forms M, N, O or P, or a pharmaceutical composition or dosage form disclosed herein.

DEFINITIONS

Within the meaning of the present invention, the term "solvent" refers to any solvent such as water and organic or inorganic solvents.

The term "room temperature" as used herein is understood to mean temperatures of about 15° C. to about 25° C.

Herein, the X-ray powder diffraction peaks of the crystalline Apremilast forms are described by their 2theta angles with a tolerance of "±0.2". In the context of the present invention, it is also possible to use a smaller tolerance of "±0.1" or even "±0.0".

Herein, Forms M and N are preferred, wherein Form N is most preferred.

Regarding the synthesis of Apremilast, reference is made to Example 1 herein, as well as to EP2276483 B1 and U.S. Pat. No. 6,962,940. Apremilast as the starting material for crystallizing any of Forms N, M, O and P of the present invention can be prepared by using any method.

Measuring Instruments, Conditions and Protocols:

UPLC

Purity and assay analysis were carried out using Ultra Performance Liquid Chromatograph Waters Acquity I-Class equipped with PDA detector. The analysis were conducted using Waters Acquity UPLC BEH C18 1.7 µm, 2.1×100 mm column, at a temperature of 60° C. The mobile phases were acetonitrile and 0.1% (v/v) ortho-phosphoric acid in water used in gradient.

GC

Determination of residual solvents were carried out using Perkin Elmer Clarus 680 Gas Chromatograph with flame-ionization detector (FID) with carrier gas split, equipped with TurboMatrix 110 Trap a headspace autosampler. The capillary column 60 m×0.32 mm ID×1.8 µm and stationary phase (6%)-cyanopropyl-phenyl-(94%)-dimethylsiloxane DB-624 Agilent Technologies at the temperature gradient were used.

KF

Water content in samples of Apremilast were determined using Mettler Toledo V30 Karl Fisher Titrator. The analysis were carried out using acetonitrile:methanol (50:50) solution and the Combi Titrant 2 Merck titrant.

XRPD

The analysis of the crystals by X-Ray diffraction was performed using X-ray Diffractometer Rigaku MiniFlex 600 in Bragg-Brentano geometry Cu Kα radiation, D/teX Ultra Detector in a range of $\lambda$=36° of 2θ angle. The wavelength of the Cu-Kα radiation used herein is $\lambda$=1.5406 Angstrom. The patterns were recorded at a tube voltage of 40 kV, tube current of 15 mA, applying a step size of 0.013° 2° with 80 s per step.

DSC

DSC analysis were carried out using DSC 1 Mettler Toledo Stare thermal analysis system at the temperature range of 25–250° C. with the gradient of 5° C./min. Melting, aluminum crucible with the capacity of 40 µl were used. Nitrogen was used as carried gas with the flow of 50 ml/min.

TGA

TGA analysis were carried out using TGA/SDTA85 Mettler Toledo Stare thermal analysis system at the temperature range of 25–220° C. with the gradient of 7° C./min. Melting, aluminum crucible with the capacity of 100 µl were used. Nitrogen was used as carried gas with the flow of 50 ml/min.

DVS

Water Vapour Sorption isotherms were obtained using a Dynamic Vapour Sorption apparatus (model: DVS—Advantage, supplier: Surface Measurement Systems Limited). The DVS apparatus consists of an ultra-microbalance housed inside a temperature-controlled cabinet. The sample was placed into a DVS sample pan under a stream of nitrogen (200 sccm) at 25° C. The humidity was increased ramping in 10% RH (relative humidity) steps from close to 0% RH to 90% RH (sorption phase). Next the humidity was decreased in a similar fashion for the desorption phase. The sample was held at each RH step for mass stabilization (dm/dt 0.02%/min) but not less than 10 minutes. Two cycles of sorption and desorption were investigated.

Dissolution Studies

Dissolution studies were performed using a Hanson SR8PLUS dissolution apparatus, according to European Pharmacopoeia apparatus, paddle method. The samples were tested in 900 mL pH 6.8 with 0.3% SLS at 37.0° C.+/−0.5° C. and the paddle rotation speed was set at 75 rpm. Dissolution study was conducted for 60 min and samples were analyzed using HPLC method.

Stability Test

A test for stability against humidity can be performed as follows: The sample is exposed to a relative humidity of 75% (+/−5%) at 50° C. (+/−2° C.) for 2 weeks. The expression "polymorphically stable" means that no conversion to another crystalline form occurs, as determined by XRPD.

The equilibrium relative humidity of a sample is measured by determining the relative humidity in % in the air above a test sample, after establishment of a humidity equilibrium in a closed/open system at a constant temperature.

The step of formulating the crystalline forms into a dosage form may be carried out by applying techniques known in the art, in particular as described herein. For example, the crystalline forms can be formulated into tablets by using direct compression, granulation processes, and spraying processes as described above. Examples are also given in the experimental part herein.

Exemplary pharmaceutically acceptable excipients which can be contemplated for use in the present invention are described in the following:

Binding agents are excipients which increase the adhesion of the active agents and excipients during granulation. Examples of binding agents are: sugars, such as sorbitol, glucose, fructose, disaccharides as saccharose, polysaccharides; acacia gum; cellulose derivatives, such as soluble celluloses like microcrystalline cellulose, methylcellulose, hydroxypropylmethylcellulose and hydroxypropylcellulose; tragacanth; polyvinylpyrrolidone, such as polyvinylpyrrolidone-vinyl acetate copolymer, or N-vinylpyrrolidone; sodium alginate and alginate derivatives and gelatin.

Disintegrants are excipients which can take up water and swell and thus improve disintegration of a tablet or granules. Examples of disintegrants are: crospovidone, croscarmellose sodium; starch (paste and pre-gelatinized), such as sodium starch glycolate, methacrylic acid polymer with divinylbenzene, potassium salt, Maltodextrin; croscarmellose sodium and low substituted hydroxypropylcellulose and crospovidone.

Lubricants are excipients which reduce the friction between excipients and compression tooling surfaces.

Examples of lubricants are magnesium stearate, magnesium fumarate, fumaric-acid, talc, steraric acid and sodium stearylfumarate.

Fillers are excipients which increase the volume of e.g. tablets. Examples of fillers are mannitol, celluloses such as microcrystalline cellulose, synthetic polymers, Ca-phosphate, inorganic calcium salts, maize starch, polyols and pregelatinzed starch.

A polymer, or a plurality of polymers may be used for coating tablets, including for example cellulose derivatives, e.g. hydroxypropylmethylcellulose, polyvinylpyrrolidones, polyethyleneglycols, polyvinylalcohols, acrylates, such as polymethacrylate, cyclodextrins and copolymers and derivatives thereof, including for example polyvinylpyrolidine-vinylacetate. In some preferred embodiments the polymer or the plurality of polymers are pH dependent enteric polymers. Such polymers include cellulose derivatives, e.g. cellulose acetate phthalate, hydroxypropyl methyl cellulose phthalates, hydroxypropyl methyl acetate succinate, hydroxypropyl methyl cellulose acetate, carboxymethylcellulose or a salt thereof, e.g the sodium salt, cellulose acetate trimellitate, hydroxypropylcellulose acetate phthalate, or polymethylacrylates, e.g. Eudragit®S.

Surfactants include but are not limited to, sorbitan fatty esters, polyoxyethylene sorbit esters, sodium laurylsulfate, sodium docedylbenzenesulfate, dioctyl sodium sulfosuccinate, sodium stearate, EDTA or vitamin E or tocol derivates.

Most preferred for preparing pharmaceutical compositions/dosage forms is the use of one or more, preferably all, of lactose monohydrate, microcrystalline cellulose, magnesium stearate and croscarmellose sodium.

Other excipients are known in the art and can be chosen by a skilled person depending on their function.

Characterization of Unsolvated Form N of Apremilast

Figure 3:
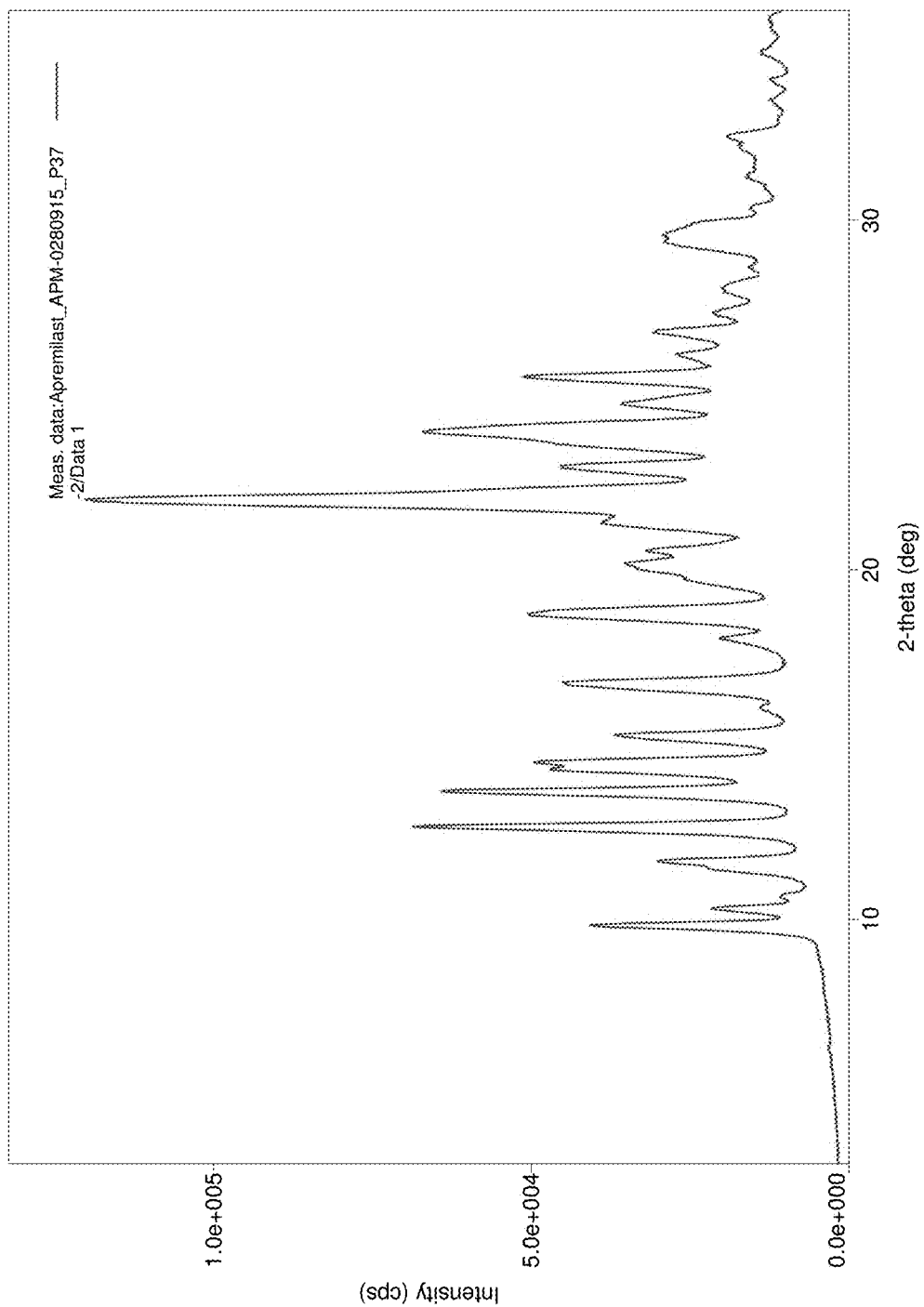
FIG. 3: The figure shows a representative XRPD pattern of Form N of Apremilast.

The preparation of Form N is described in Example 1. Crystalline Form N of Apremilast can be characterized as already described above. It has an X-ray powder diffraction pattern as depicted in FIG. 3 and as listed in Table 5 below, which shows the peak positions and their intensities.

TABLE 5

| No. | 2-theta(deg) | Rel. int. I(a.u.) |
|---|---|---|
| 1 | 9.9 | 12.95 |
| 2 | 10.34 | 6.93 |
| 3 | 10.8 | 1.53 |
| 4 | 11.7 | 26.45 |
| 5 | 11.9 | 13.80 |
| 6 | 12.7 | 25.49 |
| 7 | 13.7 | 25.29 |
| 8 | 14.4 | 15.85 |
| 9 | 14.6 | 14.71 |
| 10 | 15.3 | 16.73 |
| 11 | 16.1 | 1.93 |
| 12 | 16.7 | 20.64 |
| 13 | 16.9 | 6.38 |
| 14 | 18.1 | 6.84 |
| 15 | 18.8 | 31.17 |
| 16 | 20.2 | 27.84 |
| 17 | 20.6 | 6.89 |
| 18 | 21.4 | 10.52 |
| 19 | 22.1 | 100.00 |
| 20 | 23.0 | 15.78 |
| 21 | 23.7 | 14.79 |
| 22 | 24.0 | 43.66 |
| 23 | 24.8 | 14.19 |
| 24 | 25.6 | 25.33 |
| 25 | 26.2 | 5.25 |
| 26 | 26.8 | 17.14 |
| 27 | 28.1 | 9.92 |
| 28 | 29.4 | 17.25 |

TABLE 5-continued

| No. | 2-theta(deg) | Rel. int. I(a.u.) |
|---|---|---|
| 29 | 29.8 | 10.04 |
| 30 | 31.4 | 6.44 |
| 31 | 32.3 | 7.26 |

Figure 4:
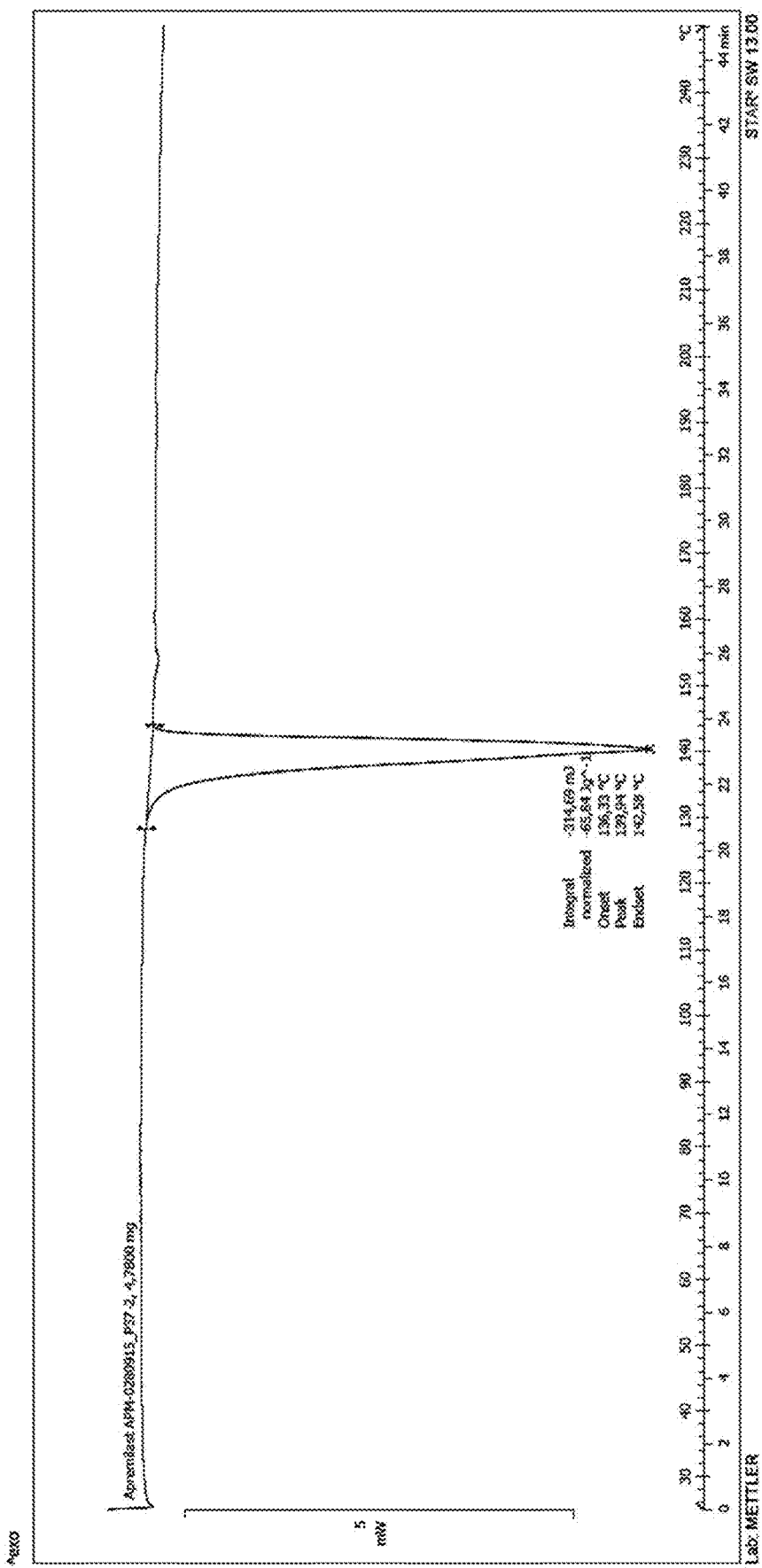
FIG. 4: The figure shows a representative DSC plot of Form N of Apremilast.

Form N of Apremilast may also (further) be characterized by thermal analysis. A representative DSC plot for Form N of Apremilast is shown in FIG. 4. The DSC plot of Form N comprises an endothermic event with an onset temperature of about 139° C., e.g. about 139° C.±2° C.

Figure 5:
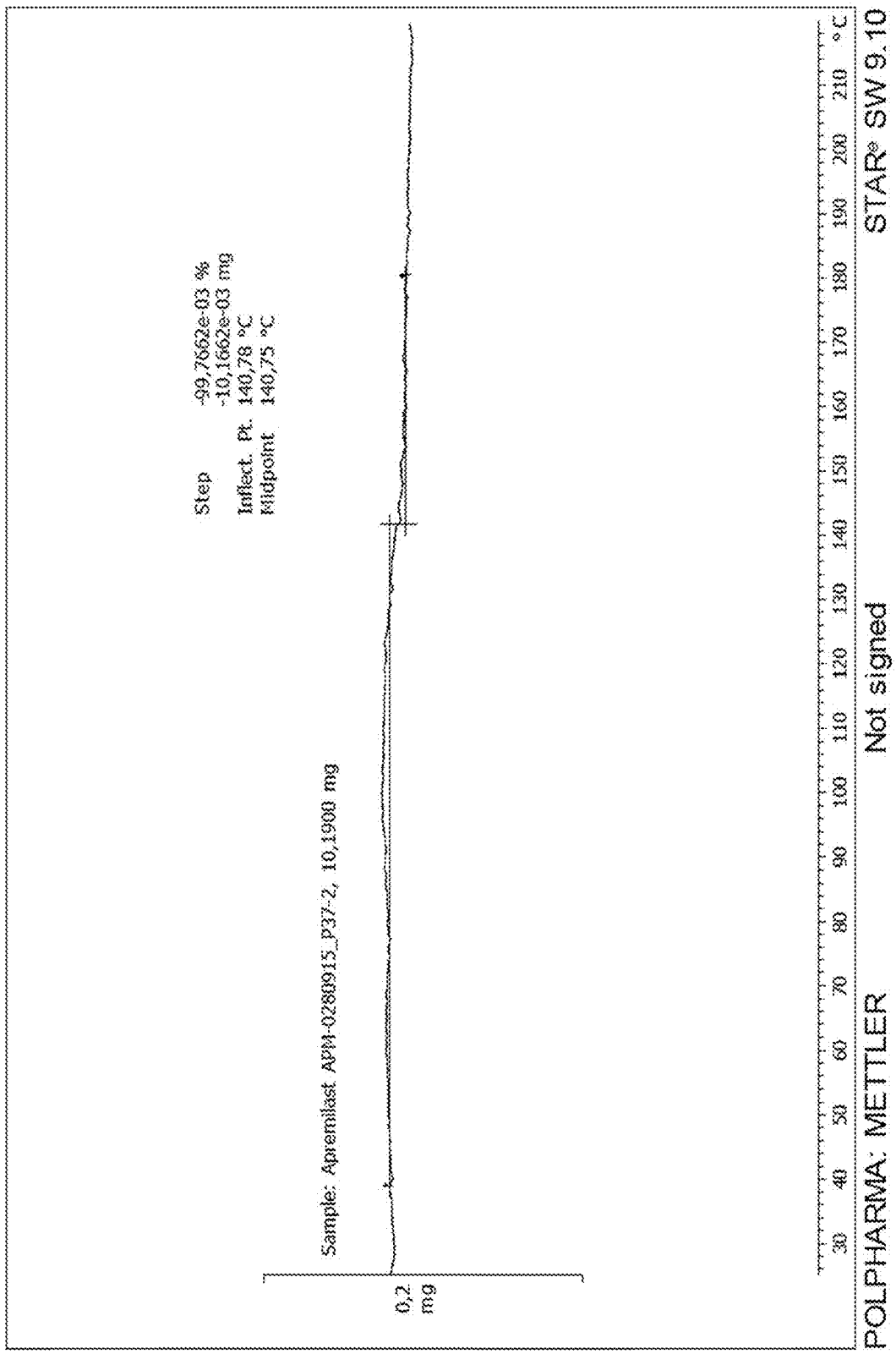
FIG. 5: The figure shows a representative thermogravimetric analysis (TGA) plot of Form N of Apremilast.

A representative TGA plot for Form N of Apremilast is shown in FIG. 5. The TGA plot of Form N shows a mass loss of less than about 0.5%, e.g., less than 0.1%, of the total mass of the sample upon heating from about 25° C. to about 220° C. Form N of Apremilast does not contain substantial amounts of either water or other solvent (confirmed by GC analysis, solvent content below 0.15%) in the crystal lattice, meaning that is at least substantially or completely unsolvated, in particular anhydrous.

Figure 6:
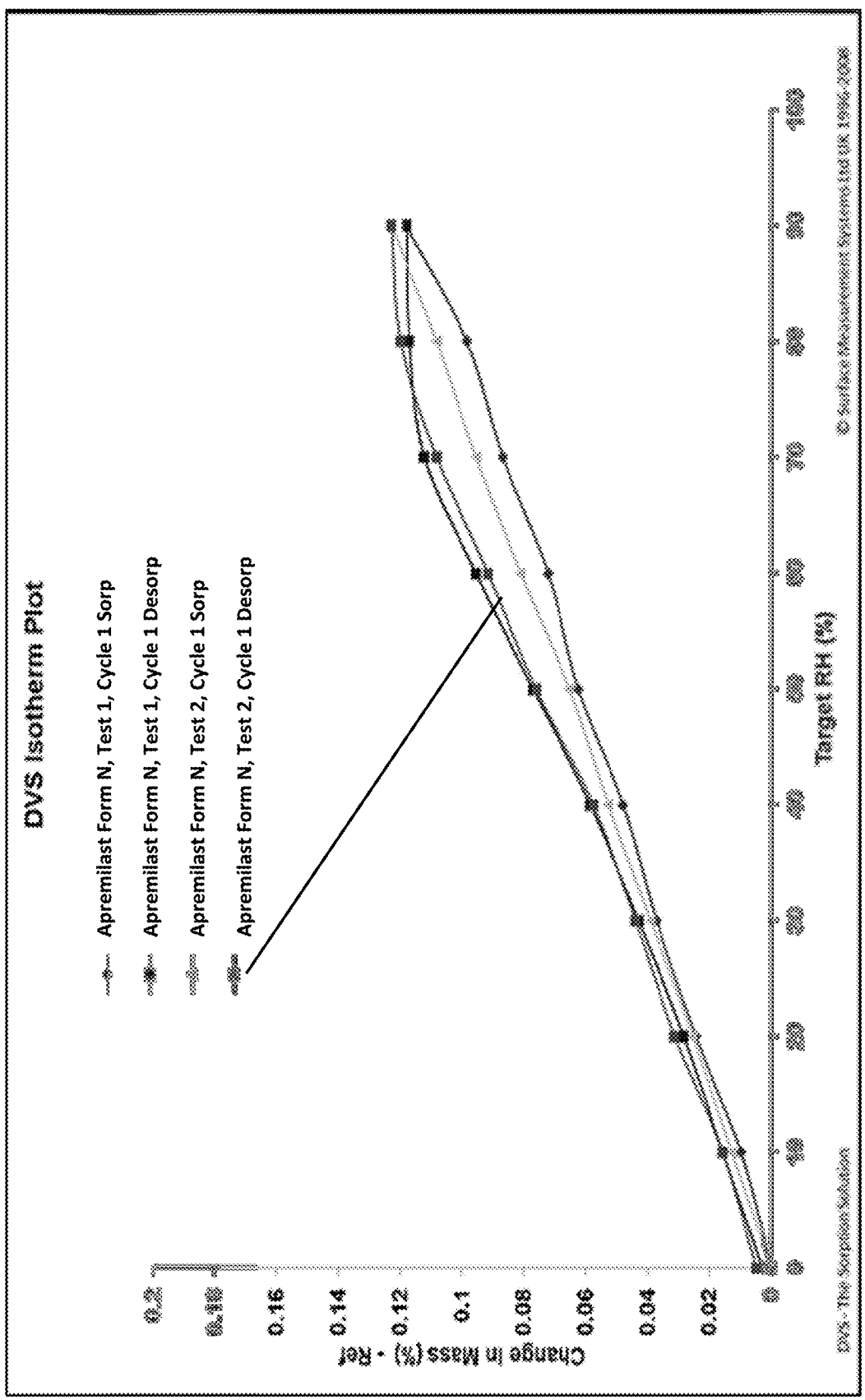
FIG. 6: The figure shows a representative Dynamic Vapour Sorption (DVS) plot of Form N of Apremilast.

Form N of Apremilast may be characterized by moisture sorption analysis. A representative moisture sorption isotherm plot is shown in FIG. 6. When RH is increased from about 0% to about 95% RH, it exhibits a mass change of less than about 0.2%, e.g., about 0.14%, of the starting amount at about 0% RH. Form N is substantially non-hygroscopic and stable with respect to humidity.

Crystalline Form N of Apremilast can be characterized by having a dissolution profile as shown in FIG. 7.

Figure 8:
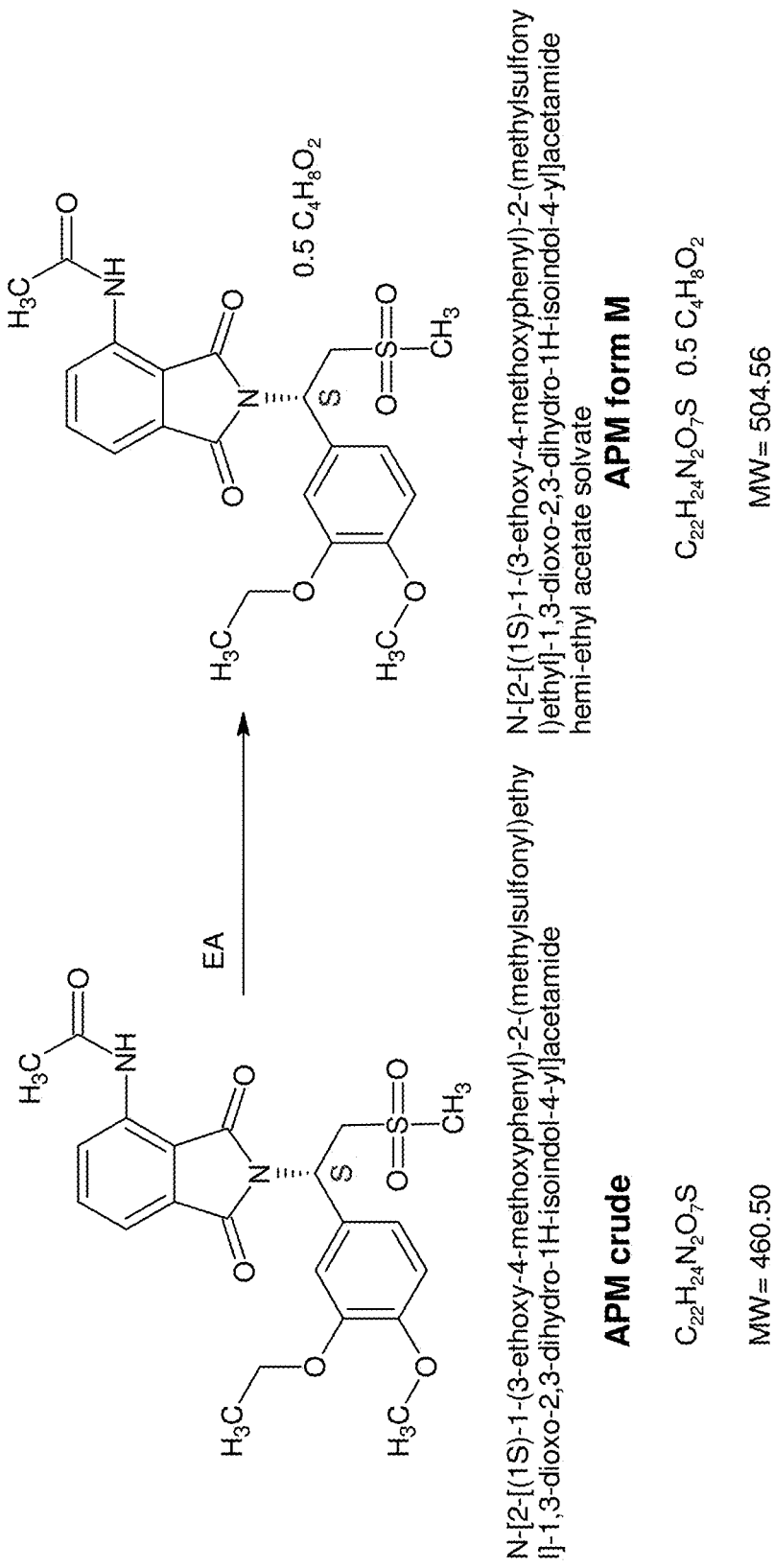
FIG. 8: The figure shows the crystallization of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM), Form M. "EA" means ethyl acetate.
Figure 9:
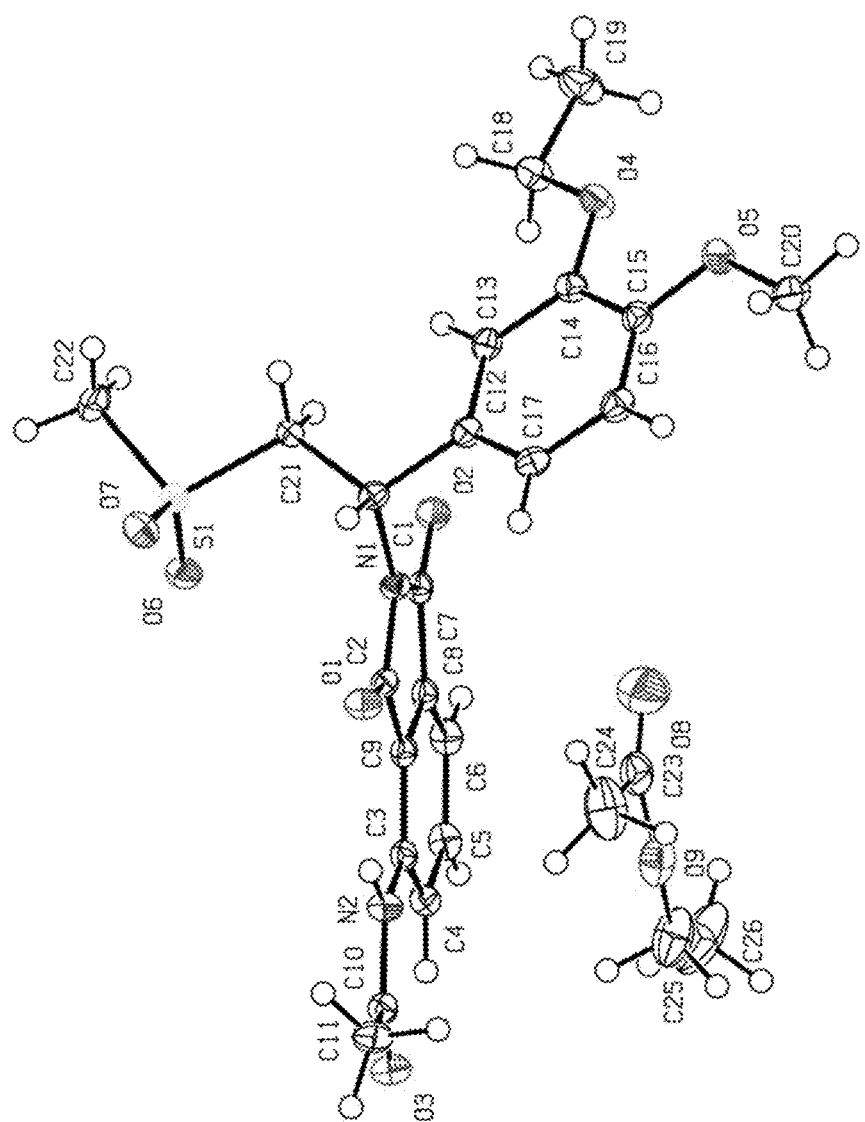
FIG. 9: The figure shows a single crystal structure of Form M of Apremilast.

Characterization of Form M (Containing Ethyl Acetate Solvent Molecules) of Apremilast The preparation of Form M is described in Example 2 (see also FIG. 8). Form M can be characterized by Single Crystal X-ray Crystallography Method. FIG. 9 shows an X-ray structure for Form M of Apremilast with the numbering scheme being used. Solvated Form M of Apremilast with ethyl acetate crystallizes in the tetragonal crystal system, in the P41212 space group. The asymmetric unit cell consists of one molecule of Apremilast and 0.5 molecule of ethyl acetate. Crystallographic data with unit cell parameters, atomic coordinates, equivalent isotropic temperature parameters for non-hydrogen atoms, bond lengths and angles are listed in the below tables.

Figure 10:
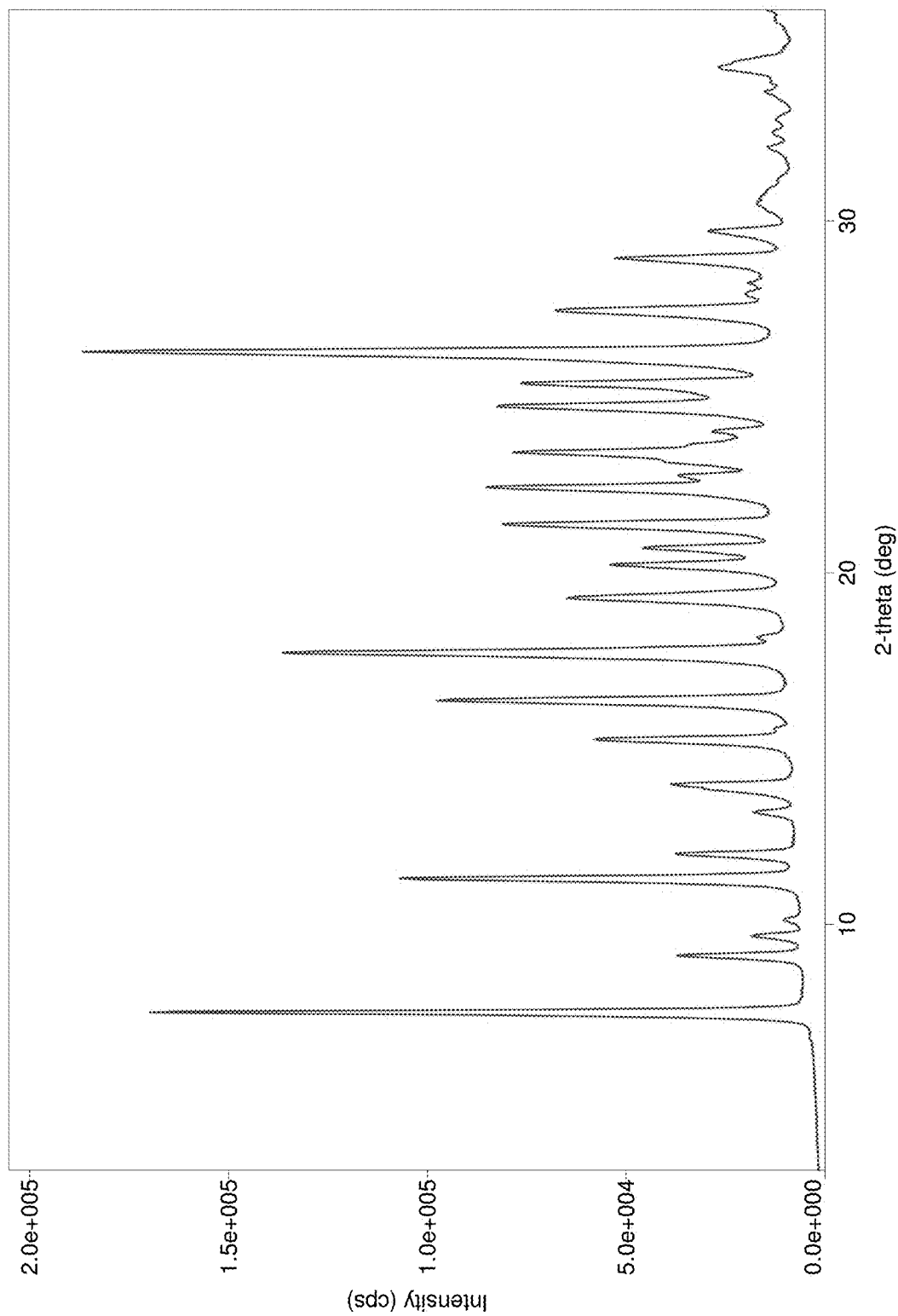
FIG. 10: The figure shows a representative XRPD pattern of Form M of Apremilast.

The crystalline Form M of Apremilast can be characterized as described above and has an X-ray powder diffraction pattern as depicted in FIG. 10 and below Table 6.

TABLE 6

| No. | 2-theta(deg) | Rel. int. I(a.u.) |
|---|---|---|
| 1 | 7.5 | 64.05 |
| 2 | 9.1 | 14.28 |
| 3 | 9.7 | 5.10 |
| 5 | 11.3 | 46.19 |
| 6 | 12.0 | 12.88 |
| 7 | 14.0 | 18.37 |
| 8 | 15.2 | 15.09 |
| 9 | 15.3 | 10.72 |
| 10 | 16.4 | 45.72 |
| 11 | 17.7 | 70.79 |
| 12 | 19.3 | 32.37 |
| 13 | 20.2 | 19.62 |
| 14 | 20.7 | 14.84 |
| 15 | 21.4 | 34.11 |
| 16 | 22.5 | 32.68 |
| 17 | 22.8 | 10.32 |
| 18 | 23.2 | 15.25 |

TABLE 6-continued

| No. | 2-theta(deg) | Rel. int. I(a.u.) |
|---|---|---|
| 19 | 23.4 | 22.12 |
| 20 | 24.7 | 34.29 |
| 21 | 25.4 | 32.30 |
| 22 | 26.3 | 100.00 |
| 23 | 27.5 | 30.53 |
| 24 | 29.0 | 20.37 |
| 25 | 29.7 | 7.97 |
| 26 | 30.5 | 4.70 |
| 27 | 34.3 | 14.62 |

Figure 11:
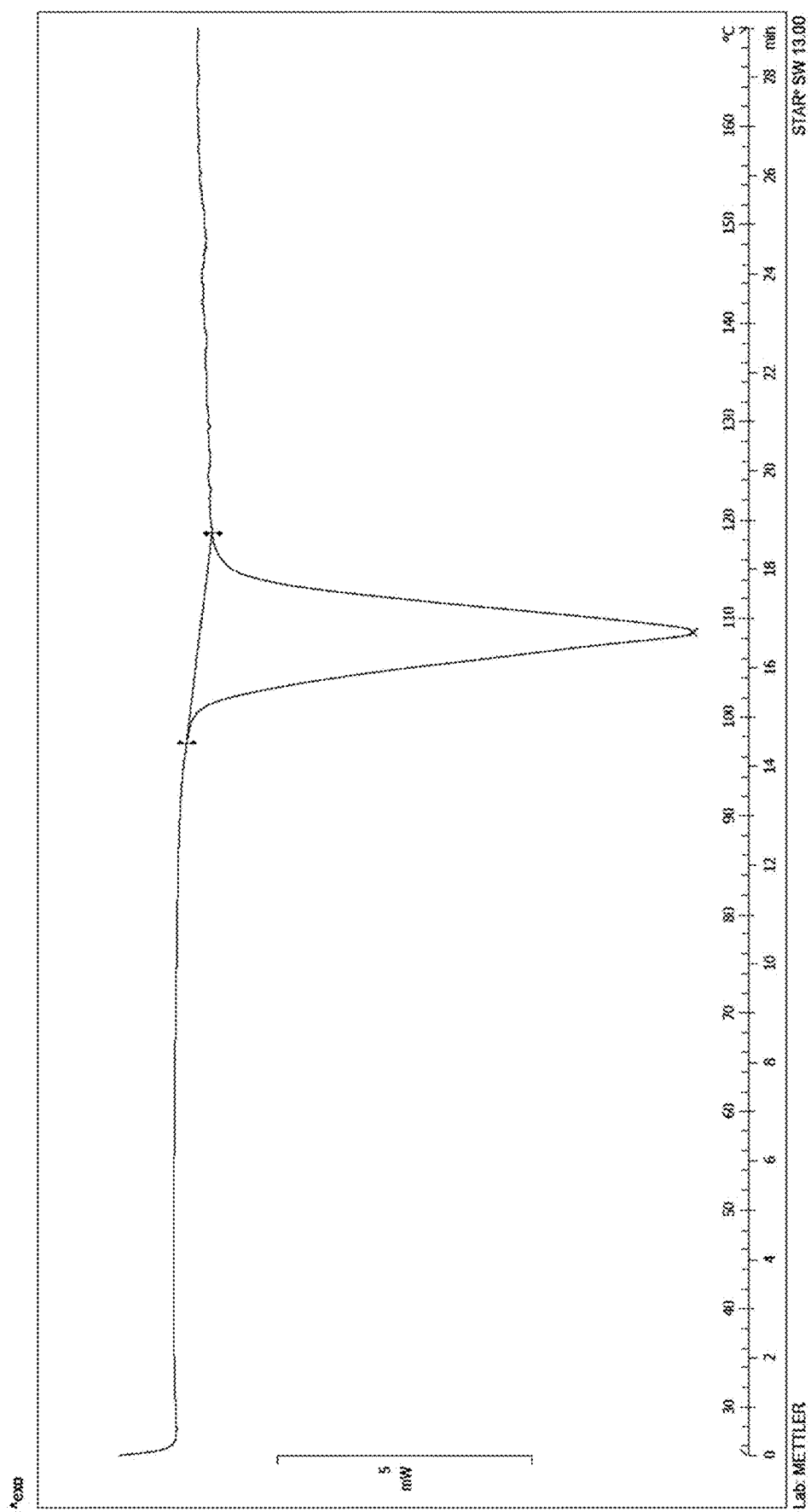
FIG. 11: The figure shows a representative differential scanning calorimeter (DSC) plot of Form M of Apremilast.

Form M of Apremilast may be also (further) characterized by thermal analysis. A representative DSC plot for Form M of Apremilast is shown in FIG. 11. The DSC plot of Form M comprises an endothermic event with an onset temperature of about 103°, e.g. about 103° C.±2° C.

Figure 12:
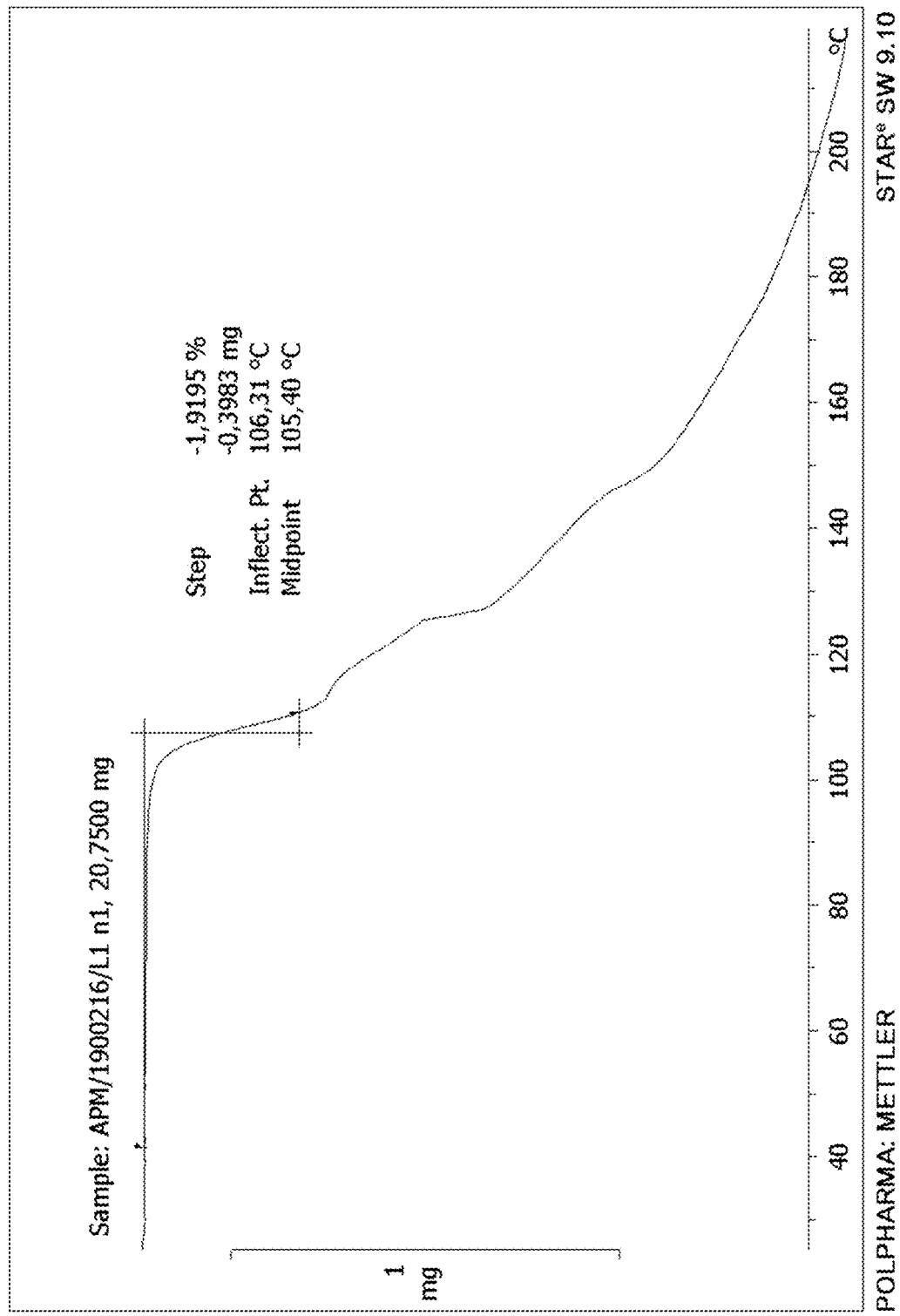
FIG. 12: The figure shows a representative TGA plot of Form M of Apremilast.

A representative TGA plot for Form M of Apremilast is shown in FIG. 12. The TGA plot of Form M shows a mass loss of more than 2%, e.g., about 2%, of the total mass of the sample upon heating from about 25° C. to 110° C. and about 8.5% of the total mass of the sample upon heating from about 25° C. to 220° C. The TGA mass loss event comprises the loss of the solvent ethyl acetate, as indicated, e.g., by GC analysis. Form M hemi-ethyl acetate is a solvated modification of Apremilast. The crystal lattice of Form M comprises 0.5 molar equivalent of ethyl acetate per one mole of Apremilast (as confirmed by SC-XRD method).

Figure 13:
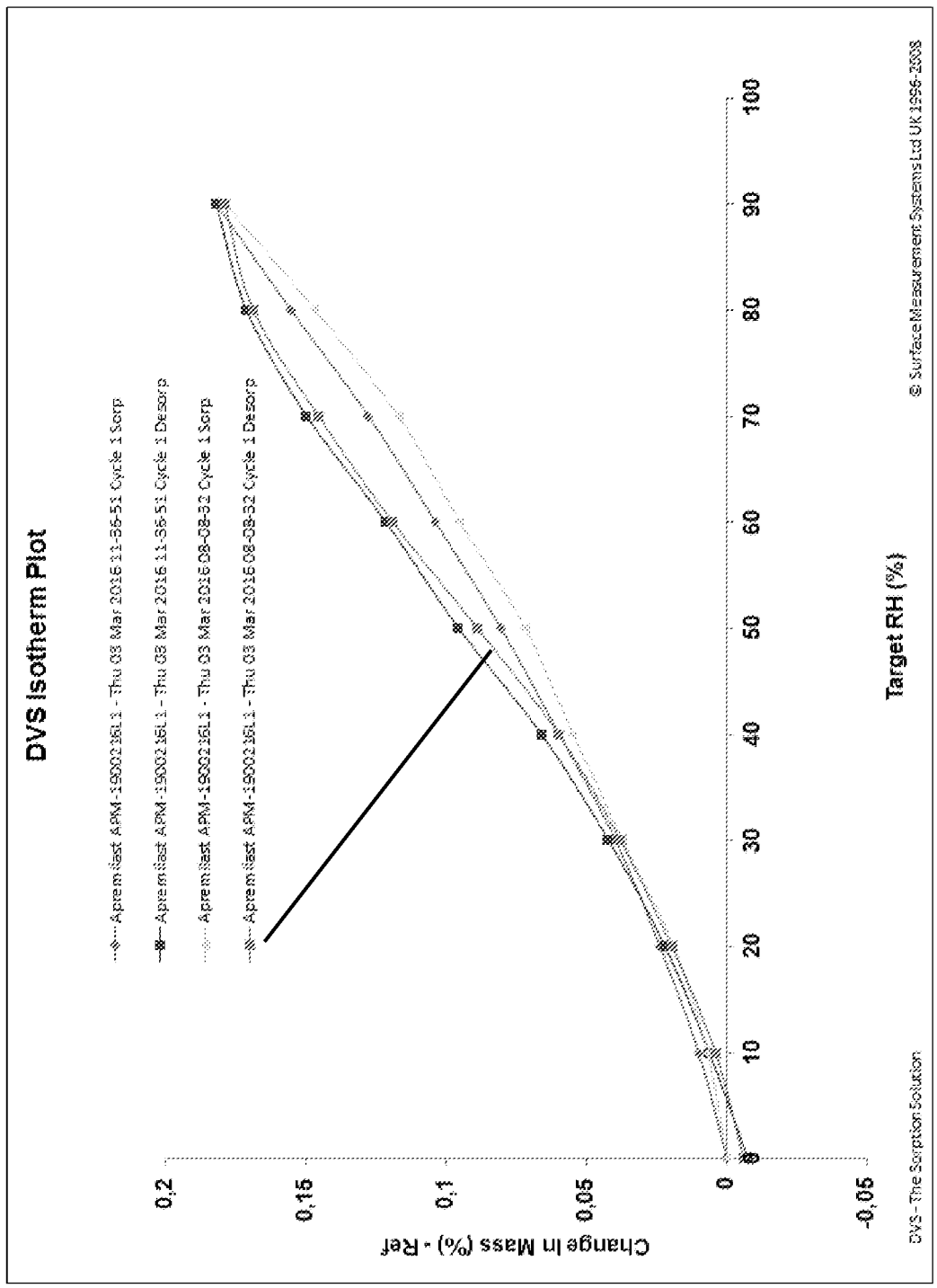
FIG. 13: The figure shows a representative DVS plot of Form M of Apremilast.

Form M of Apremilast may be characterized by moisture sorption analysis. A representative moisture sorption isotherm plot is shown in FIG. 13. When RH is increased from about 0% to about 95% RH, it exhibits a mass change of less than about 0.5%, e.g., about 0.2%, of the starting amount at about 0% RH.

TABLE 7

Crystal data of form M
Crystallographic data

| Empirical formula | $C_{22}H_{24}N_2O_7S \cdot 0.5C_4H_8O_2$ |
|---|---|
| Formula weight | 504.54 g/mol |
| Temperature | 100 K |
| Crystal system | tetragonal |
| Space group | $P4_12_12$ |
| Unit cell dimensions | a = b = 12.8568(2) Å |
| | c = 29.5578(4) Å |
| | α = β = γ = 90° |
| F(000) | 2128 |
| Volume | 4885.8(2) Å$^3$ |
| Z | 8 |
| Calculated density | 1.372 g/cm$^3$ |
| Theta range for data collection | 3°-67.0° |
| R index | R = 2.17% |
| Flack's parameter | 0.002(2) |
| CuK$_α$ radiation | 1.54178 Å |
| Crystal size | 0.08 × 0.15 × 0.15 mm |

Table 8 shows the atomic coordinates and equivalent isotropic temperature parameters for non-hydrogen atoms.

TABLE 8

| Atom | x | y | z | U$_{(eq)}$ |
|---|---|---|---|---|
| S1 | 0.83730(3) | 0.59584(3) | 0.03680(2) | 0.0169(1) |
| O1 | 0.76019(9) | 0.51831(10) | 0.16683(4) | 0.0195(3) |
| O2 | 0.52954(9) | 0.59614(10) | 0.05373(4) | 0.0203(4) |
| O3 | 0.67987(10) | 0.80017(10) | 0.28944(4) | 0.0236(4) |
| O4 | 0.45702(10) | 0.24102(9) | −0.01799(4) | 0.0213(4) |
| O5 | 0.43894(10) | 0.10382(10) | 0.04670(4) | 0.0241(4) |
| O6 | 0.78901(10) | 0.68947(10) | 0.05381(4) | 0.0230(4) |
| O7 | 0.92439(10) | 0.55422(10) | 0.06169(4) | 0.0245(4) |

TABLE 8-continued

| Atom | x | y | z | U$_{(eq)}$ |
|---|---|---|---|---|
| N1 | 0.65426(11) | 0.53560(11) | 0.10364(4) | 0.0156(4) |
| N2 | 0.70488(12) | 0.67896(12) | 0.23418(5) | 0.0176(4) |
| C1 | 0.70188(13) | 0.45355(13) | 0.07554(5) | 0.0156(4) |
| C2 | 0.69084(13) | 0.56304(13) | 0.14650(5) | 0.0154(4) |
| C3 | 0.63399(13) | 0.71095(13) | 0.20106(6) | 0.0162(5) |
| C4 | 0.56458(13) | 0.79512(13) | 0.20505(6) | 0.0186(5) |
| C5 | 0.49557(14) | 0.81876(14) | 0.17024(6) | 0.0210(5) |
| C6 | 0.49049(14) | 0.76071(14) | 0.13025(6) | 0.0199(5) |
| C7 | 0.57478(13) | 0.60225(14) | 0.08976(5) | 0.0160(5) |
| C8 | 0.55921(13) | 0.67855(14) | 0.12680(5) | 0.0167(5) |
| O8* | 0.4686(3) | 0.4457(3) | 0.18671(13) | 0.0537(12) |
| O9 | 0.4558(13) | 0.5428(15) | 0.2516(13) | 0.034(3) |
| C9 | 0.62940(13) | 0.65449(13) | 0.16096(6) | 0.0159(5) |
| C10 | 0.72204(14) | 0.72079(14) | 0.27633(6) | 0.0185(5) |
| C11 | 0.79494(15) | 0.65812(15) | 0.30524(6) | 0.0235(5) |
| C12 | 0.62969(13) | 0.36120(13) | 0.06785(6) | 0.0169(5) |
| C13 | 0.57627(13) | 0.34662(13) | 0.02698(6) | 0.0173(5) |
| C14 | 0.51267(13) | 0.26071(14) | 0.02067(6) | 0.0177(5) |
| C15 | 0.50207(14) | 0.18718(13) | 0.05566(6) | 0.0188(5) |
| C16 | 0.55460(15) | 0.20242(14) | 0.09619(6) | 0.0206(5) |
| C17 | 0.61802(14) | 0.28928(14) | 0.10212(6) | 0.0192(5) |
| C18 | 0.46104(15) | 0.31989(14) | −0.05253(6) | 0.0219(5) |
| C19 | 0.38534(18) | 0.29084(17) | −0.08938(7) | 0.0316(6) |
| C20 | 0.41835(19) | 0.03591(15) | 0.08380(7) | 0.0321(7) |
| C21 | 0.74102(13) | 0.49802(13) | 0.03055(5) | 0.0162(4) |
| C22 | 0.87563(16) | 0.61725(15) | −0.01960(6) | 0.0265(6) |
| C23* | 0.4981(4) | 0.4676(3) | 0.22374(15) | 0.0337(14) |
| C24* | 0.5890(16) | 0.4185(15) | 0.2521(9) | 0.045(3) |
| C25* | 0.4036(4) | 0.6321(4) | 0.27060(18) | 0.0423(17) |
| C26* | 0.3346(9) | 0.6785(7) | 0.2613(3) | 0.075(4) |

Table 9 shows the Bond lengths (A) in Form M of Apremilast.

TABLE 9

| S1 | —O6 | 1.445(1) |
|---|---|---|
| O9 | —C25 | 1.44(2) |
| S1 | —O7 | 1.443(1) |
| O9 | —C23 | 1.38(3) |
| S1 | —C21 | 1.774(2) |
| C10 | —C11 | 1.503(3) |
| S1 | —C22 | 1.760(2) |
| C12 | —C17 | 1.380(2) |
| O1 | —C2 | 1.219(2) |
| C12 | —C13 | 1.402(2) |
| O2 | —C7 | 1.216(2) |
| C13 | —C14 | 1.387(2) |
| O3 | —C10 | 1.219(2) |
| C14 | —C15 | 1.408(2) |
| O4 | —C14 | 1.372(2) |
| C15 | —C16 | 1.389(3) |
| O4 | —C18 | 1.440(2) |
| C16 | —C17 | 1.394(3) |
| O5 | —C15 | 1.370(2) |
| C18 | —C19 | 1.508(3) |
| O5 | —C20 | 1.427(2) |
| N1 | —C1 | 1.476(2) |
| N1 | —C2 | 1.397(2) |
| N1 | —C7 | 1.395(2 |
| N2 | —C3 | 1.399(2) |
| N2 | —C10 | 1.375(2) |
| C1 | —C12 | 1.524(2) |
| C1 | —C21 | 1.533(2) |
| C2 | —C9 | 1.480(2) |
| C3 | —C9 | 1.391(2) |
| C3 | —C4 | 1.408(2) |
| C4 | —C5 | 1.392(3) |
| C5 | —C6 | 1.399(3) |
| C6 | —C8 | 1.381(3) |
| C7 | —C8 | 1.484(2) |
| C8 | —C9 | 1.389(2) |
| O8 | —C23 | 1.192(6) |
| C23 | —C24 | 1.57(2) |
| C25 | —C26 | 1.104(12) |

Table 10 shows the Bond Angles (Q) in Form M of Apremilast.

TABLE 10

| | | | | | | | |
|---|---|---|---|---|---|---|---|
| O6 | —S1 | —O7 | 117.72(8) | N1 | —C7 | —C8 | 106.73(13) |
| O6 | —S1 | —C21 | 109.09(8) | C6 | —C8 | —C7 | 130.29(15) |
| O6 | —S1 | —C22 | 108.64(8) | C7 | —C8 | —C9 | 107.55(15) |
| O7 | —S1 | —C21 | 109.37(8) | C6 | —C8 | —C9 | 122.16(15) |
| O7 | —S1 | —C22 | 108.89(9) | C2 | —C9 | —C8 | 108.29(15) |
| C21 | —S1 | —C22 | 101.98(8) | C2 | —C9 | —C3 | 129.65(15) |
| C14 | —O4 | —C18 | 116.23(13) | C3 | —C9 | —C8 | 122.05(16) |
| C15 | —O5 | —C20 | 116.11(14) | C23 | —O9 | —C25 | 166(3) |
| C1 | —N1 | —C2 | 123.47(13) | O3 | —C10 | —C11 | 123.07(16) |
| C1 | —N1 | —C7 | 125.27(12) | O3 | —C10 | —N2 | 122.97(16) |
| C2 | —N1 | —C7 | 110.99(13) | N2 | —C10 | —C11 | 113.93(15) |
| C3 | —N2 | —C10 | 128.57(15) | C13 | —C12 | —C17 | 119.32(16) |
| N1 | —C1 | —C12 | 112.84(13) | C1 | —C12 | —C17 | 118.61(15) |
| N1 | —C1 | —C21 | 110.97(13) | C1 | —C12 | —C13 | 122.07(15) |
| C12 | —C1 | —C21 | 111.17(13) | C12 | —C13 | —C14 | 120.74(16) |
| O1 | —C2 | —N1 | 125.04(15) | C13 | —C14 | —C15 | 119.54(16) |
| O1 | —C2 | —C9 | 128.52(15) | O4 | —C14 | —C15 | 115.95(15) |
| N1 | —C2 | —C9 | 106.44(14) | O4 | —C14 | —C15 | 124.51(16) |
| O5 | —C15 | —C14 | 116.14(15) | C14 | —C15 | —C16 | 119.46(16) |
| N2 | —C3 | —C4 | 125.47(16) | O5 | —C15 | —C16 | 124.40(16) |
| C4 | —C3 | —C9 | 116.47(16) | C15 | —C16 | —C17 | 120.39(16) |
| N2 | —C3 | —C9 | 118.06(15) | C12 | —C17 | —C16 | 120.55(16) |
| C3 | —C4 | —C5 | 120.66(16) | O4 | —C18 | —C19 | 108.34(15) |
| C4 | —C5 | —C6 | 122.52(16) | S1 | —C21 | —C1 | 113.78(11) |
| C5 | —C6 | —C8 | 116.13(16) | O2 | —C7 | —N1 | 124.62(15) |
| O2 | —C7 | —C8 | 128.64(16) | O8 | —C23 | —O9 | 126.0(13) |
| O8 | —C23 | —C24 | 129.2(9) | O9 | —C23 | —C24 | 104.8(15) |
| O9 | —C25 | —C26 | 135.0(14) | | | | |

The crystal structure is additionally stabilized by the presence of strong N—H . . . O hydrogen bonds and many weaker C—H . . . O interactions (Table 11). Table 11 shows the inter- and intramolecular hydrogen bonds (Å, °).

TABLE 11

| Donor --- H . . . Acceptor | [ARU] | D - H | H . . . A | D . . . A | D - H . . . A |
|---|---|---|---|---|---|
| N(2)—H(2) . . . O(1) | [ ] | 0.81(2) | 2.29(2) | 2.956(2) | 139.3(19) |
| C(4)—H(4) . . . O(3) | [ ] | 0.95 | 2.30 | 2.902(2) | 120 |
| C(13)—H(13) . . . O(2) | [6555.01] | 0.95 | 2.41 | 3.360(2) | 176 |
| C(16)—H(16) . . . O(7) | [7645.01] | 0.95 | 2.41 | 3.334(2) | 163 |
| C(17)—H(17) . . . O(6) | [7645.01] | 0.95 | 2.52 | 3.287(2) | 138 |
| C(20)—H(201) . . . O(3) | [4454.01] | 0.98 | 2.48 | 3.424(2) | 163 |
| C(21)—H(211) . . . O(2) | [6555.01] | 0.99 | 2.28 | 3.137(2) | 145 |
| C(21)—H(212) . . . O(3) | [7645.01] | 0.99 | 2.45 | 3.433(2) | 172 |
| C(22)—H(221) . . . O(1) | [4564.01] | 0.98 | 2.35 | 3.062(2) | 129 |
| C(22)—H(222) . . . O(6) | [6555.01] | 0.98 | 2.55 | 3.410(2) | 147 |
| Symmetry code [ARU] | | | | | |

[6555.] = [7_555] = y, x, –z
[7645.] = [5_645] = 3/2 – x, –1/2 + y, 1/4 – z
[4564.] = [3_564] = 1/2 + y, 3/2 – x, –1/4 + z
[4454.] = [3_454] = –1/2 + y, 1/2 – x, –1/4 + z

Figure 14:
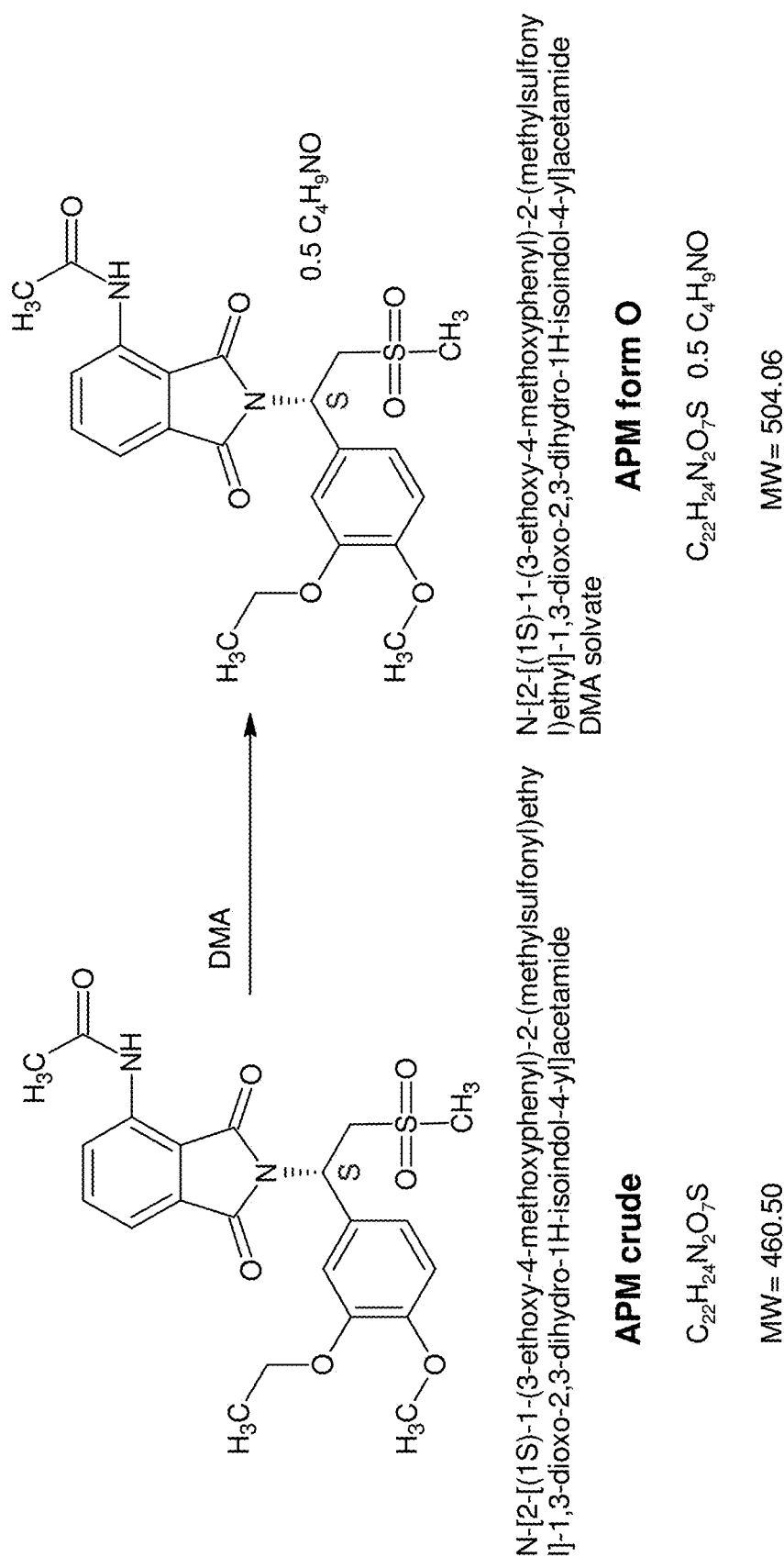
FIG. 14: The figure shows the crystallization of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM) as a hemi dimethylacetamide solvate (Form O).
Figure 15:
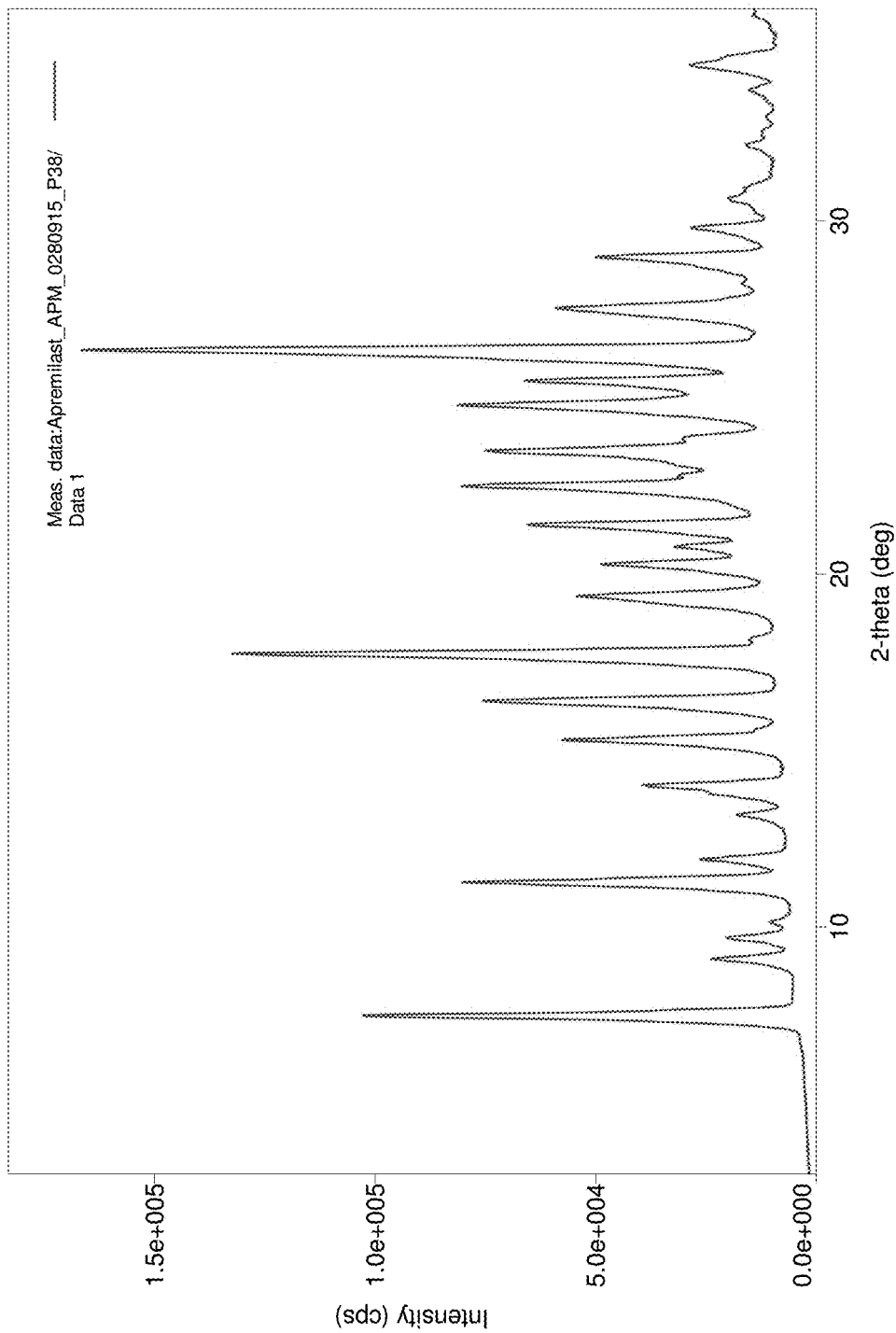
FIG. 15: The figure shows a representative XRPD pattern of Form O of Apremilast.

Characterization of Form O (containing dimethyl acetamide solvent molecules) of Apremilast The preparation of Form O is described in Example 3 (see also FIG. 14). Crystalline Form O of Apremilast can be characterized as already described above. It has an X-ray powder diffraction pattern as depicted in FIG. 15 and as listed in Table 12 below.

TABLE 12

| Peak positions and their intensities | | |
|---|---|---|
| No. | 2-theta(deg) | Rel. int. I(a.u.) |
| 1 | 7.5 | 56.54 |
| 2 | 9.1 | 11.02 |

TABLE 12-continued

| Peak positions and their intensities | | |
|---|---|---|
| No. | 2-theta(deg) | Rel. int. I(a.u.) |
| 3 | 9.7 | 9.57 |
| 4 | 10.1 | 3.10 |
| 5 | 11.2 | 45.57 |
| 6 | 11.9 | 12.37 |
| 7 | 13.2 | 5.17 |
| 8 | 13.8 | 11.97 |
| 9 | 14.0 | 10.67 |
| 10 | 15.3 | 35.90 |
| 11 | 16.4 | 44.85 |
| 12 | 17.7 | 87.42 |
| 13 | 19.2 | 9.21 |

TABLE 12-continued

Peak positions and their intensities

| No. | 2-theta(deg) | Rel. int. I(a.u.) |
|---|---|---|
| 14 | 19.4 | 20.61 |
| 15 | 20.3 | 16.88 |
| 16 | 20.8 | 5.83 |
| 17 | 21.4 | 24.81 |
| 18 | 22.5 | 33.63 |
| 19 | 22.8 | 8.80 |
| 20 | 23.5 | 29.97 |
| 21 | 23.9 | 3.30 |
| 22 | 24.8 | 38.26 |
| 23 | 25.5 | 25.94 |
| 24 | 26.4 | 100.00 |
| 25 | 27.5 | 34.55 |
| 26 | 28.5 | 5.62 |
| 27 | 29.0 | 21.83 |
| 28 | 29.8 | 9.96 |

Figure 16:
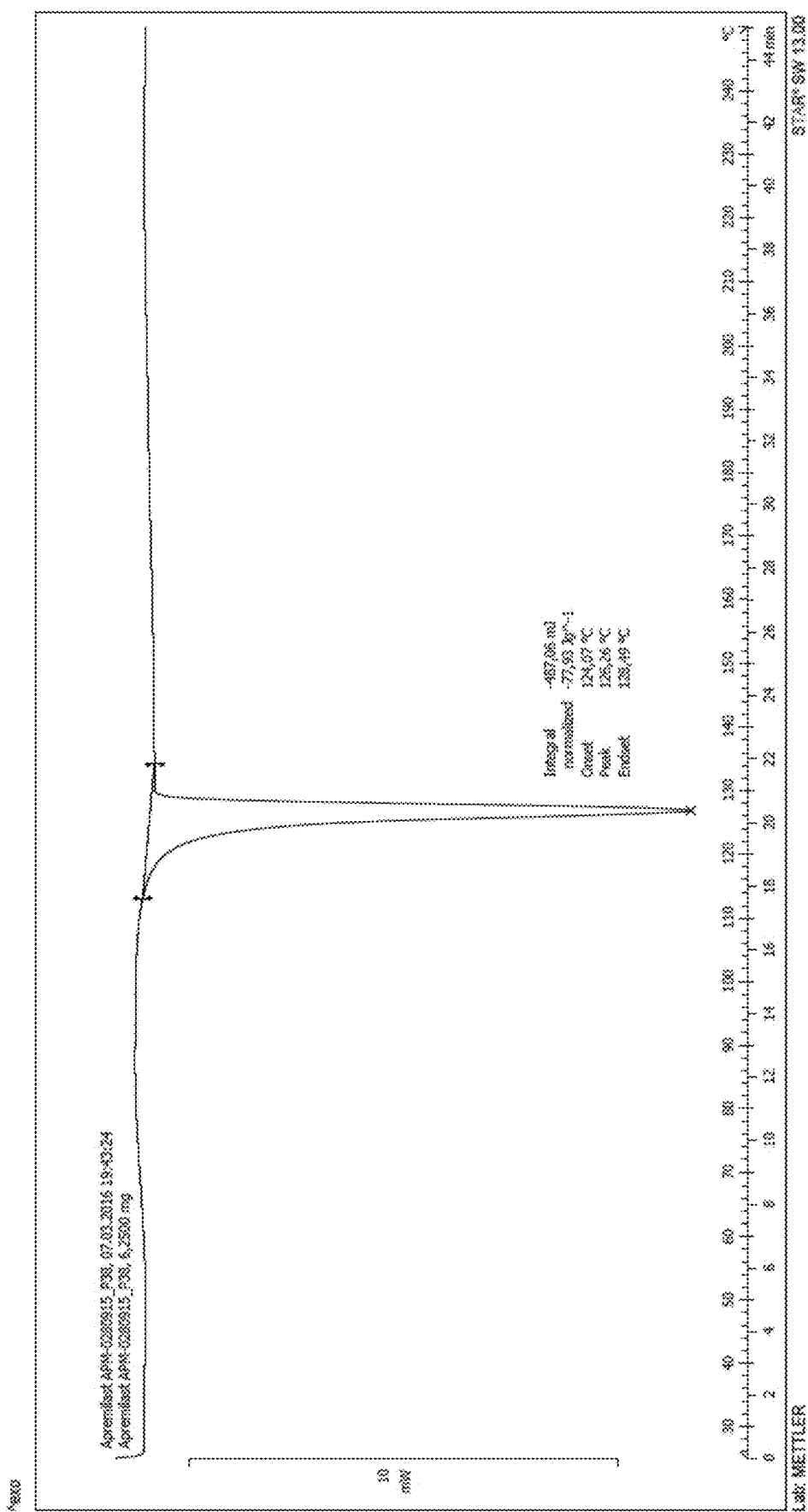
FIG. 16: The figure shows a representative DSC plot of Form O of Apremilast.

Form O of Apremilast may be also (further) characterized by thermal analysis. A representative DSC plot for Form O of Apremilast is shown in FIG. 16. The DSC plot of Form O comprises an endothermic event with an onset temperature of about 124° C., e.g. about 124° C.±2° C.

Figure 17:
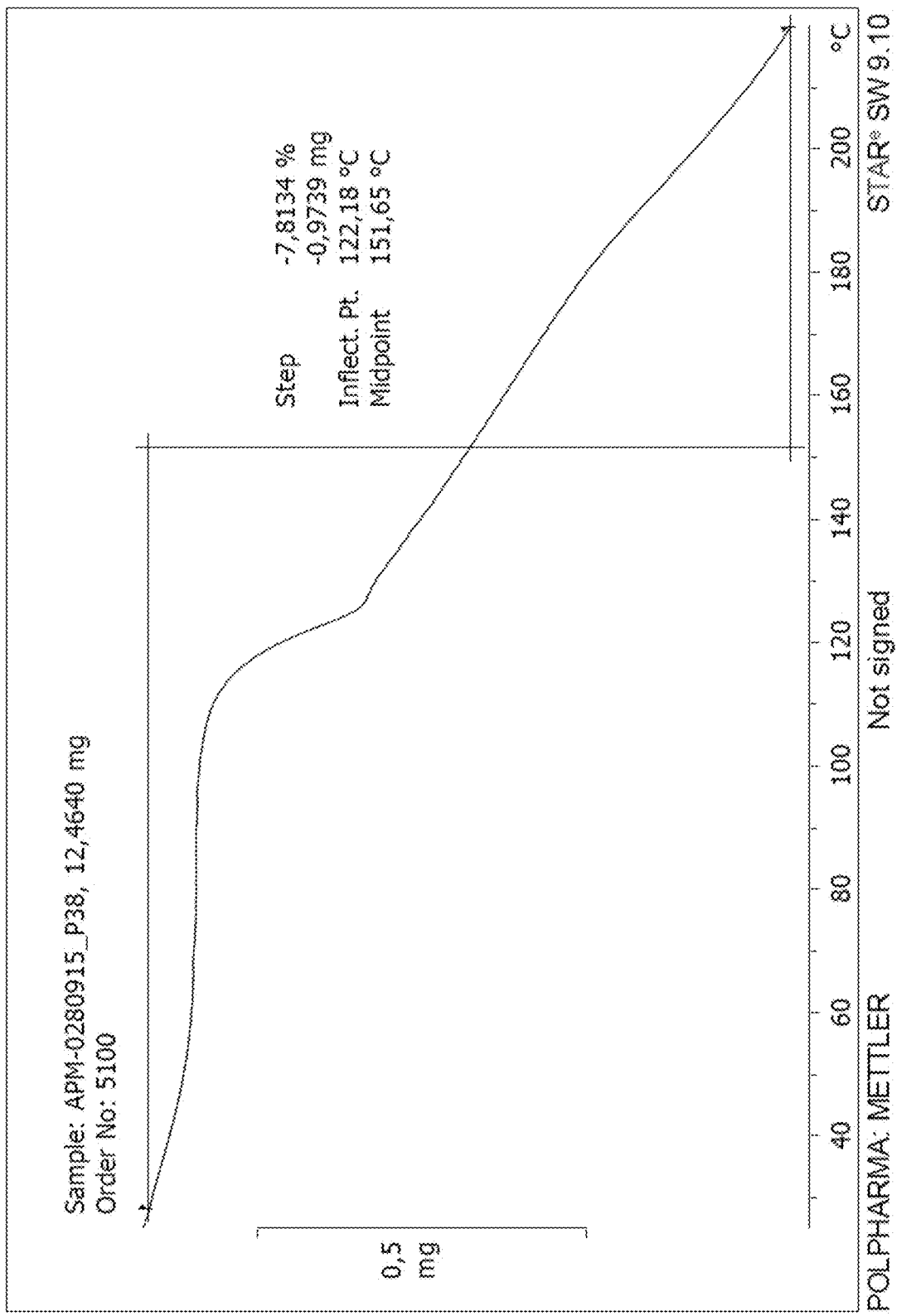
FIG. 17: The figure shows a representative TGA plot of Form O of Apremilast.

A representative TGA plot for Form O of Apremilast is shown in FIG. 17. The TGA plot of Form O comprises a mass loss of more than about 7%, e.g., 7.8%, of the total mass of the sample upon heating from about 25° C. to about 220° C. The TGA mass loss event comprises the loss of the solvent dimethyl acetamide, as indicated, e.g., by GC analysis. Form O is the DMA solvated modification of Apremilast. The crystal lattice of Form O comprises about 0.5 molar equivalent of DMA per one mole of Apremilast.

Characterization of Form P (Containing DMF Solvent Molecules) of Apremilast

Figure 18:
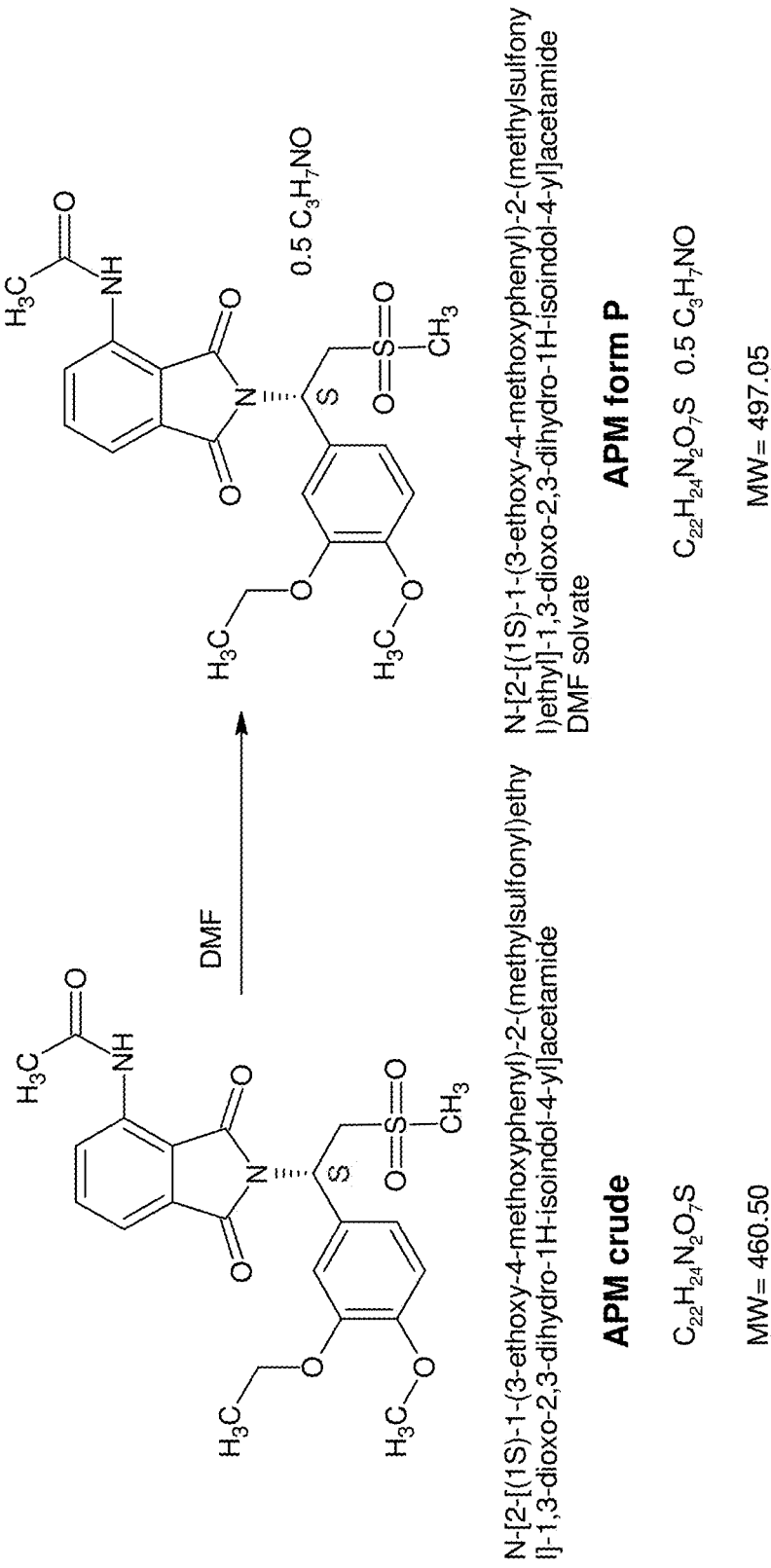
FIG. 18: The figure shows the crystallization of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM), as a hemi dimethylformamide solvate (Form P). "DMF" means dimethylformamide.
Figure 19:
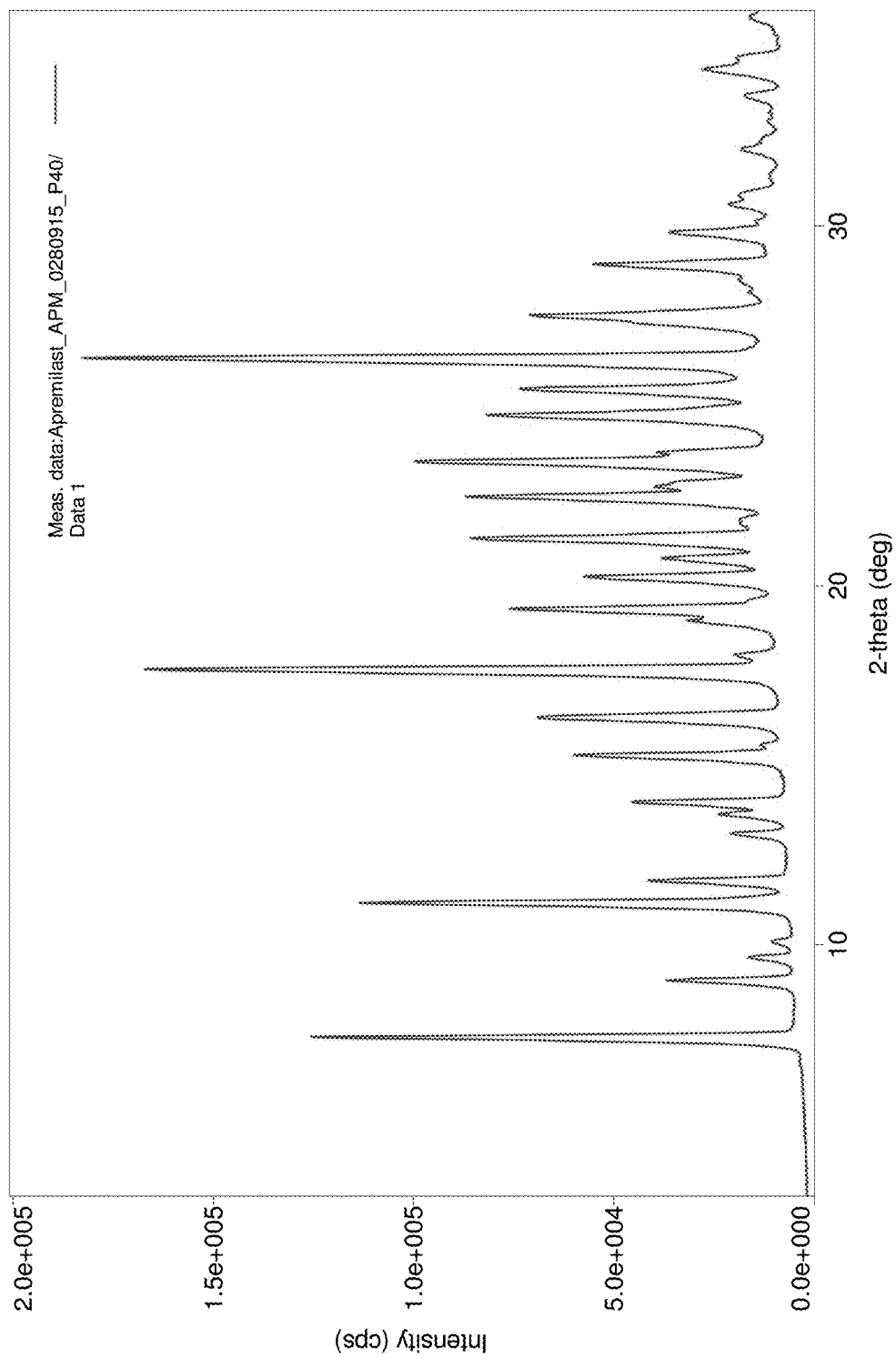
FIG. 19: The figure shows a representative XRPD pattern of Form P of Apremilast.

The preparation of Form P is described in Example 4 and FIG. 18. Crystalline Form P of Apremilast can be characterized as already described above. It has an X-ray powder diffraction pattern as depicted in FIG. 19 and as listed in Table 13 below. Table 13 shows the peak positions and their intensities.

TABLE 13

| No. | 2-theta(deg) | Rel. int. I(a.u.) |
|---|---|---|
| 1 | 7.4 | 54.31 |
| 2 | 9.0 | 13.80 |
| 3 | 9.7 | 4.28 |
| 5 | 11.2 | 51.06 |
| 6 | 11.8 | 14.59 |
| 7 | 13.1 | 6.81 |
| 8 | 13.7 | 8.46 |
| 9 | 14.0 | 19.62 |
| 10 | 15.3 | 31.07 |
| 11 | 16.3 | 39.11 |
| 12 | 17.7 | 83.78 |
| 13 | 18.1 | 4.14 |
| 14 | 19.0 | 10.30 |
| 15 | 19.3 | 28.62 |
| 16 | 20.3 | 21.45 |
| 17 | 20.8 | 10.15 |
| 18 | 21.3 | 38.78 |
| 19 | 22.5 | 37.15 |
| 20 | 22.7 | 8.84 |
| 21 | 22.9 | 4.65 |
| 22 | 23.5 | 41.81 |
| 23 | 23.7 | 12.41 |
| 24 | 24.7 | 41.49 |
| 25 | 25.5 | 31.97 |
| 26 | 26.3 | 100.00 |
| 27 | 27.3 | 22.14 |

TABLE 13-continued

| No. | 2-theta(deg) | Rel. int. I(a.u.) |
|---|---|---|
| 28 | 27.5 | 21.75 |
| 29 | 28.9 | 23.03 |

Figure 20:
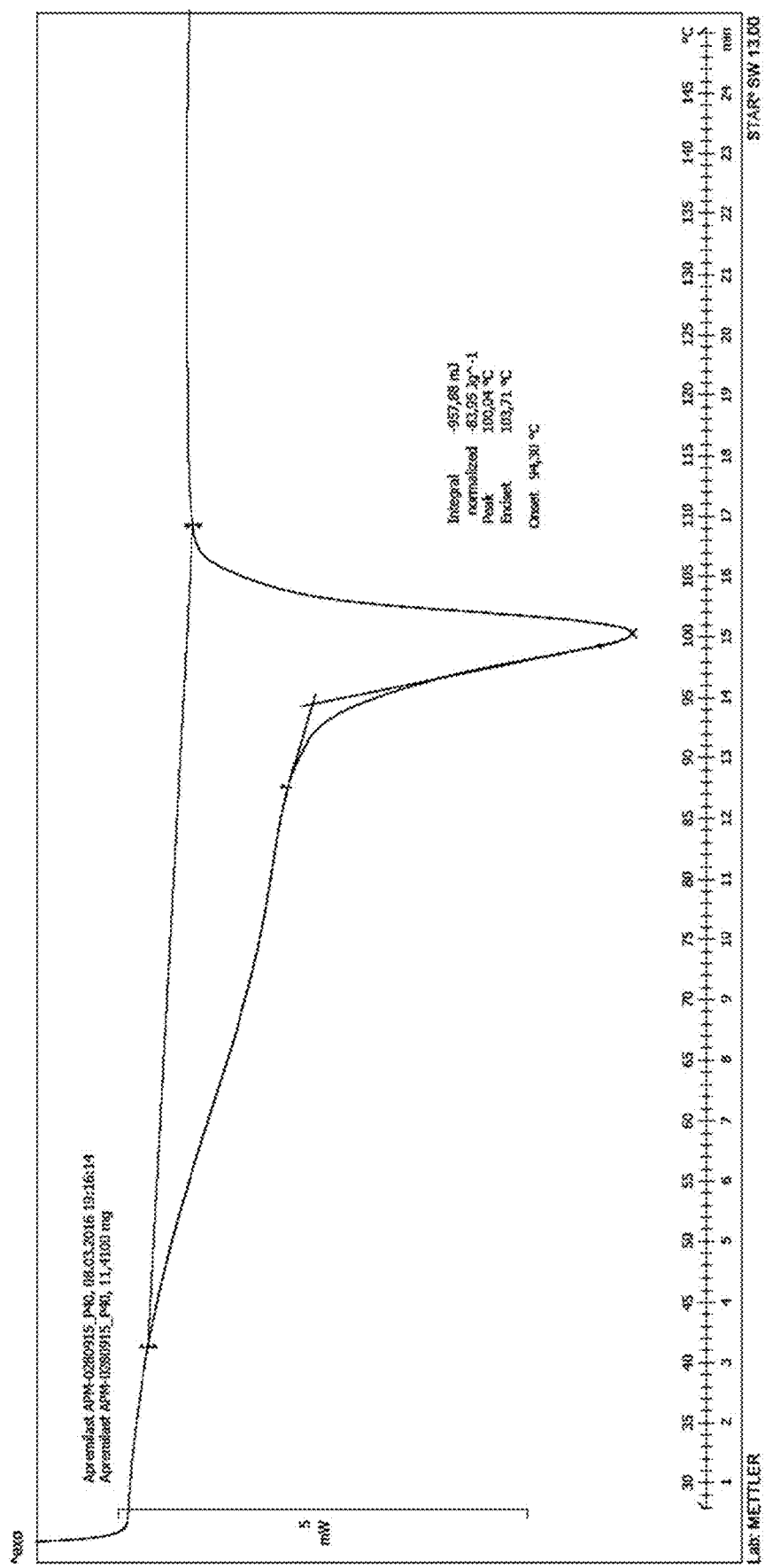
FIG. 20: The figure shows a representative DSC plot of Form P of Apremilast.

Form P of Apremilast may be also (further) characterized by thermal analysis. A representative DSC plot for Form P of Apremilast is shown in FIG. 20. The DSC plot of Form P comprises an endothermic event with an onset temperature of about 94° C., e.g. about 94° C.±2° C.

Figure 21:
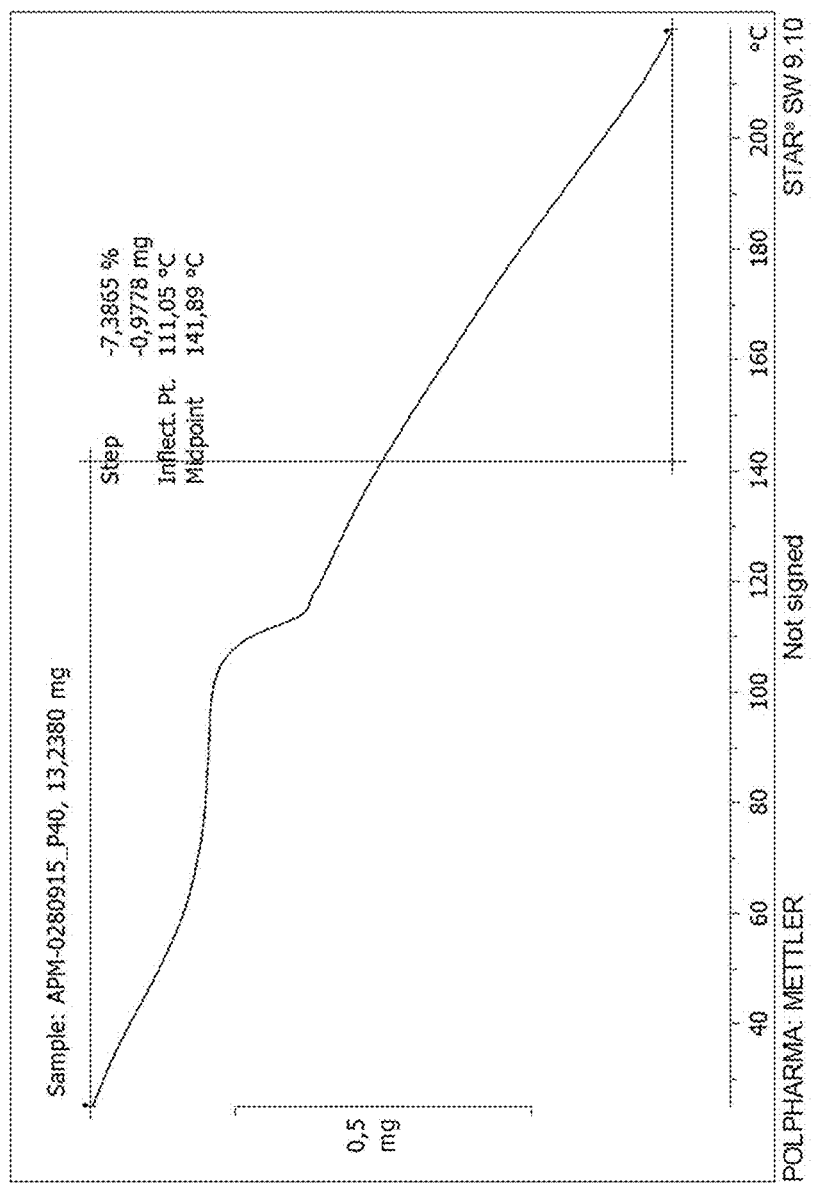
FIG. 21: The figure shows a representative TGA plot of Form P of Apremilast.

A representative TGA plot for Form P of Apremilast is shown in FIG. 21. The TGA plot of Form P comprises a mass loss of more than about 7%, e.g., 7.4%, of the total mass of the sample upon heating from about 25° C. to about 220° C. The TGA mass loss event comprises the loss of the solvent DMF, as indicated, e.g., by GC analysis. Form P is the DMF solvated modification of Apremilast. The crystal lattice of Form P comprises about 0.5 or less molar equivalents of DMF per one mole of Apremilast.

The following examples describe the present invention in detail, but are not to be construed to be in any way limiting for the present invention.

Example 1—Preparation of Unsolvated Form N of Apremilast 1.1 Preparation of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM)

The below preparation serves as a non-limiting example for preparing APM. Any other method for preparing APM is also suitable in the context of the present invention.

Figure 1:
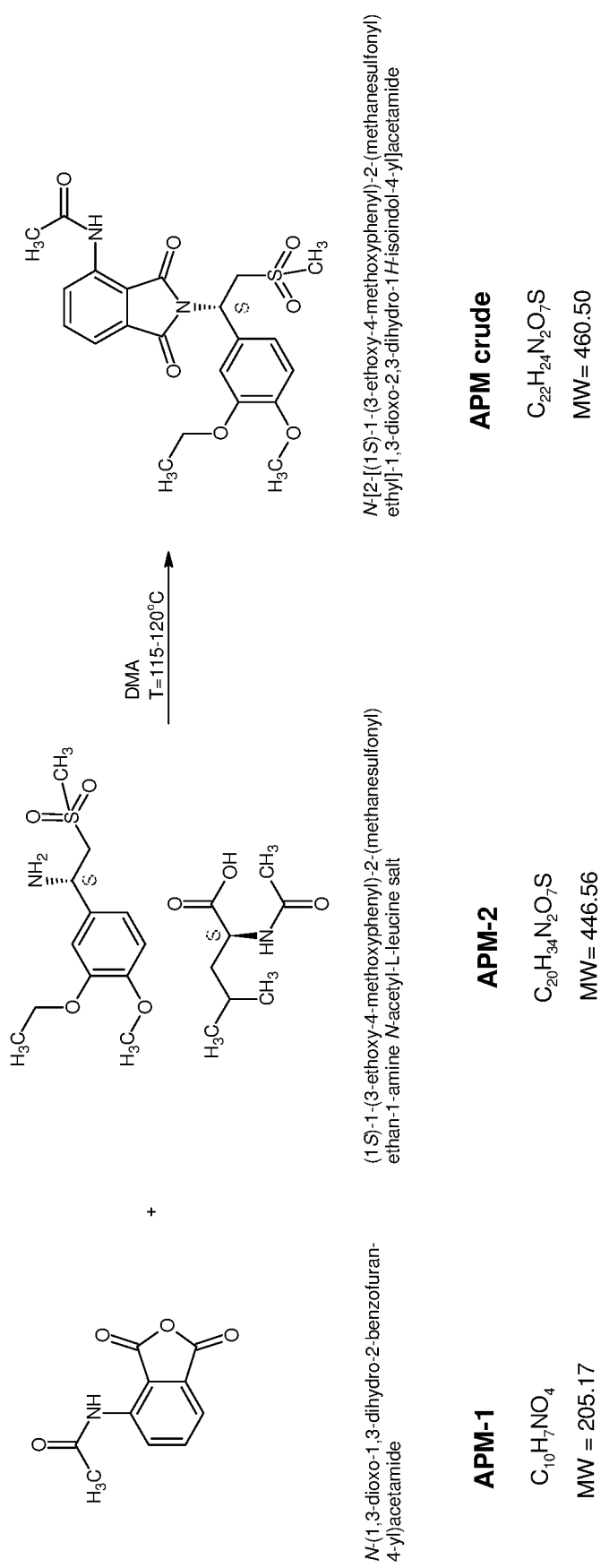
FIG. 1: The figure shows the preparation of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (Apremilast, APM).

Reference is made to FIG. 1. APM-1 (9.65 g) was dissolved in dimethylacetamide (100 ml) at ambient temperature. Then APM-2 (20 g) was suspended and dimethylacetamide (100 ml) was charged. After warming up of the suspension to the temperature 110-120° C. under flow of inert gas the reaction mixture was stirred between 2-4 hours.

When the reaction was finished (after 2-4 h at 110-120° C.) the solution was cooled down to a temperature of 20-25° C. Ethyl acetate (180 ml) and water (180 ml) were added to the reaction mixture and the reaction mass was stirred for 10 min at 20-30° C. After separation, the ethyl acetate phase was left and the water phase was extracted with ethyl acetate (2×50 ml). The combined ethyl acetate phases were washed with 8% NaHCO$_3$ solution (2×50 ml), 1N HCl (2×50 ml), and water (1×50 ml). The organic solvent was evaporated under reduced pressure (200-30 mbar) at 35° C. giving compound APM (as an oil residue left after ethyl acetate distillation).

1.2 Crystallization of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM)

Crystallization—Option I

Figure 2:
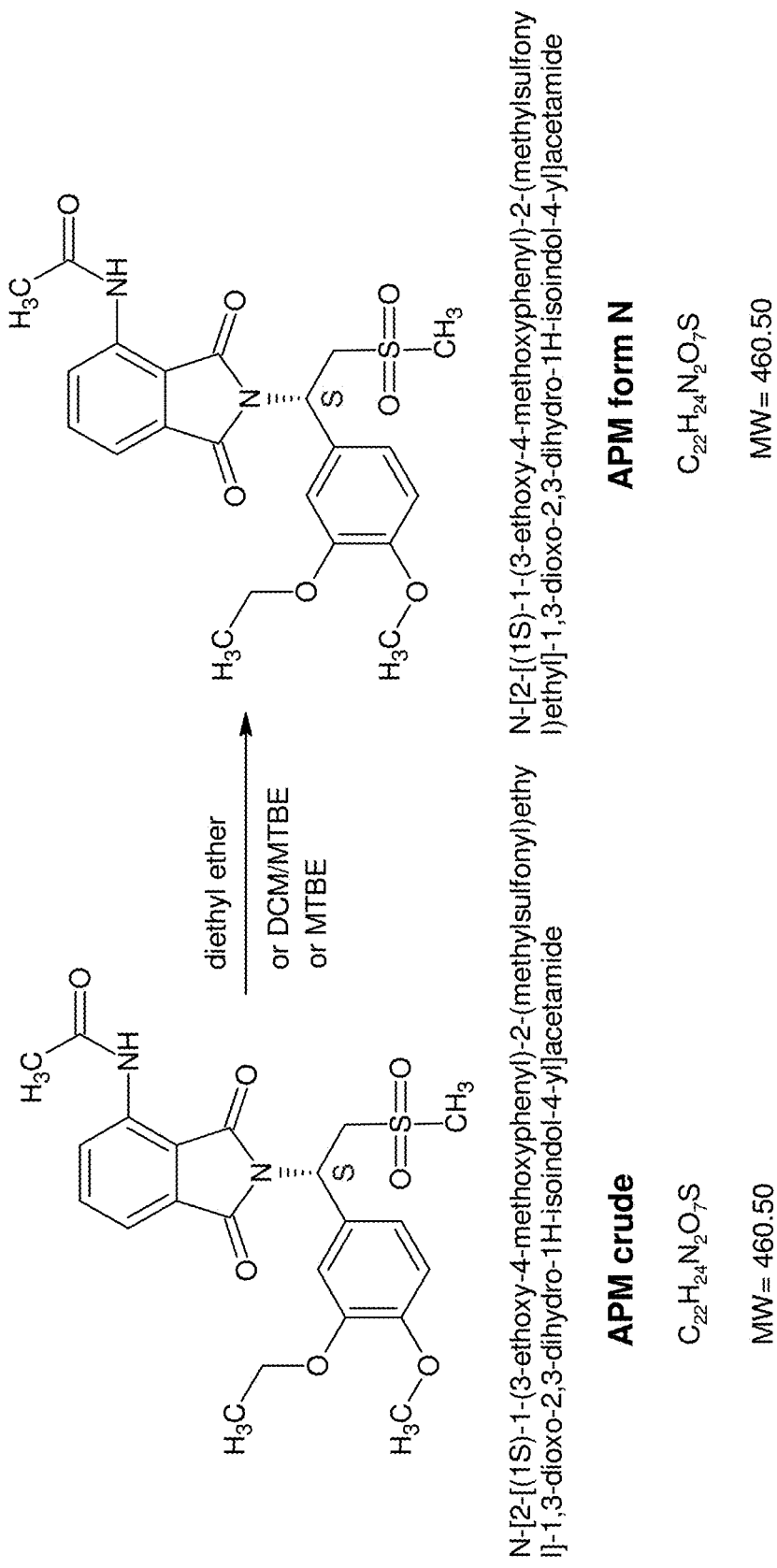
FIG. 2: The figure shows the crystallization of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM).

Reference is made to FIG. 2. For crystallization, APM in any form and prepared by any method (e.g. any known literature method), for example the method of above Example 1.1, can be used.

10 g of Apremilast were suspended in diethyl ether (200 ml) and stirred for 12 h at 25±5° C. to give a white to cream color suspension. Obtained solid was filtered under reduced pressure and dried at 85° C. and gave product APM Form N (as confirmed by XRPD, DSC and TGA) with purity above 99.90% (80-90% yield).

Crystallization—Option II

Reference is made to FIG. 2. 10 g of Apremilast were dissolved in dichloromethane (30 ml) and stirred for 30 min at 25±5° C. until a clear solution was obtained. Then, methyl tert butyl ether (200 ml) was added under stirring and seeds of Form N were added. The mass was stirred for 12 h at 25±5° C. to give a white to cream color suspension. Obtained solid was filtered under reduced pressure and dried at 85° C. gave product APM Form N (as confirmed by XRPD, DSC and TGA) with purity above 99.90% (90-95% yield).

Crystallization—Option III

Reference is made to FIG. 2. The product 10 g (APM as an oil residue left after ethyl acetate distillation) was suspended in methyl tert-butyl ether (MTBE) (1000 ml) at 20±5° C. and 0.5 g of Apremilast N seeds was charged. Crystallization mixture was vigorously stirred for 16 h at 20±5° C. to give a white to cream color suspension. Obtained solid was filtered under reduced pressure and dried at 85° C. gave product APM form N (as confirmed by XRPD, DSC and TGA) with purity above 99.90% (80-90% yield)

Example 2—Preparation of Form M of Apremilast

Crystallization of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM) Form M as the hemi ethyl acetate solvate is shown in FIG. 8:

10 g Apremilast were dissolved in ethyl acetate (52 ml) and heated to 77° C. The solution was stirred for 30 min at boiling temperature and then cooled down to −5 to −10° C. The mass was stirred for 3-6 h at about −5 to −10° C. to give a white to cream color suspension. The obtained solid was filtered under reduced pressure and the cake was washed with cold ethyl acetate (2×5 ml). Drying at reduced pressure at 50° C. gave product APM hemi-ethyl acetate form (as confirmed by XRPD, DSC, GC and TGA) with a purity of above 99.90% (88-92% yield).

Example 3—Preparation of Form O of Apremilast

Crystallization of N-[2-[(1S)-1-(3-ethoxy-4-methoxyphenyl)-2-(methylsulfonyl)ethyl]-1,3-dioxo-2,3-dihydro-1H-isoindol-4-yl]acetamide) (APM) Form O as the hemi DMA solvate is shown in FIG. 14.

10 g of Apremilast were dissolved in dimethyl acetamide (40 ml) and stirred for 30 min at 25±5° C. until a clear solution was obtained. The solution was stirred for 72 h at 25±5° C. to give a white to cream color suspension. The obtained solid was filtered under reduced pressure and dried at 50° C., which gave product APM Form O (as confirmed by XRPD, DSC and TGA) with purity above 99.90% (70-80% yield).

Example 4—Preparation of Form P of Apremilast

Reference is made to FIG. 18. 10 g of Apremilast were dissolved in dimethyl formamide (30 ml) and stirred for 30 min at 25±5° C. until a clear solution was obtained. The solution was stirred for 72 h at 25±5° C. to give a white to cream color suspension. The obtained solid was filtered under reduced pressure and dried at 50° C., which gave product APM Form P (as confirmed by XRPD, DSC and TGA) with a purity of above 99.90% (70-80% yield).

Example 5—Stability Testings with Tablets Containing Form B (Prior Art)

Tablets comprising Form B were prepared as follows:

Apremilast, lactose monohydrate, microcrystalline cellulose, croscarmellose sodium were passed through a 0.425 mm sieve. The ingredients from the sieving step are mixed in a blender for 15 min at 25 RPM (rotations per minute). Magnesium stearate is added and the mixture is mixed for 5 min at 12 RPM. The resulting blend is compressed using a single punch machine equipped with an oval punch (14×8 mm) at a compression force of 7 kN. The composition of the tablets is shown in Table 14.

TABLE 14

| (Sample 001) | | |
|---|---|---|
| Ingredient | mg/tabl | %/tabl |
| Apremilast (Form B) | 30.00 | 10.00 |
| Lactose monohydrate | 171.00 | 57.00 |
| Microcrystalline cellulose | 85.50 | 28.50 |
| Croscarmellose sodium | 11.25 | 3.75 |
| Magnesium stearate | 2.25 | 0.75 |
| total: | 300.00 | 100.00 |

Stability Results after 2 Weeks (Conditions Either Closed or Open):

TABLE 15

| Sample 001 initial | Form B |
|---|---|
| 50° C./75% RH close | not changed |
| 50° C./75% RH open | not changed |
| RT/70-75% RH open | not changed |

Example 6—Stability Testings with Tablets Containing an Amorphous Form

Tablets comprising an amorphous form of APM were prepared as follows:

Apremilast (Form M) was dissolved in acetone. Lactose monohydrate, microcrystalline cellulose, croscarmellose sodium were passed through a 0.425 mm sieve. The ingredients from the previous step were added to a fluid bed granulator (equipped with top spray nozzle) and granulated by spraying the solution. The obtained granulate was dried. Magnesium stearate was added and mixed for 5 min at 12 RPM. The blend was compressed using a single punch machine equipped with oval punch (14×8 mm) at a compression force of 7 kN.

TABLE 16

| (Sample 002) | | |
|---|---|---|
| Ingredient | mg/tabl | %/tabl |
| Apremilast (amorphous form) | 30.00 | 10.00 |
| Lactose monohydrate | 171.00 | 57.00 |
| Microcrystalline cellulose | 85.50 | 28.50 |

TABLE 16-continued (Sample 002)

| Ingredient | mg/tabl | %/tabl |
|---|---|---|
| Croscarmellose sodium | 11.25 | 3.75 |
| Magnesium stearate | 2.25 | 0.75 |
| total: | 300.00 | 100.00 |

Stability Results after 2 Weeks (Conditions Closed or Open):

TABLE 17

| Sample 002 initial | Amorphous |
|---|---|
| 50° C./75% RH close | changed into B |
| 50° C./75% RH open | changed into B |
| RT/70-75% RH open | not changed |

Example 8—Stability Testings with Tablets Containing Form N

Sample 004 comprising Form N was prepared as follows:

Apremilast Form N, lactose monohydrate, microcrystalline cellulose, croscarmellose sodium were passed through a 0.425 mm sieve. The ingredients from the previous step were mixed in a blender for 15 min at 25 RPM. Magnesium stearate was added and the resulting mixture was mixed for 5 min at 12 RPM. The resulting blend was compressed using a single punch machine equipped with oval punch (14×8 mm) at a compression force of 7 kN

TABLE 18

| Ingredient | mg/tabl | %/tabl |
|---|---|---|
| Apremilast (Form N) | 30.00 | 10.00 |
| Lactose monohydrate | 171.00 | 57.00 |
| Microcrystalline cellulose | 85.50 | 28.50 |
| Croscarmellose sodium | 11.25 | 3.75 |
| Magnesium stearate | 2.25 | 0.75 |
| total: | 300.00 | 100.00 |

Stability Results after 2 Weeks:

TABLE 19

| Sample 004 initial | Form N |
|---|---|
| 50° C./75% RH close | not changed |
| 50° C./75% RH open | not changed |
| RT/70-75% RH open | not changed |

Example 9—Dissolution Properties of Tablets with Form B (Prior Art) and Form N The dissolution profile of Apremilast Form N and Form B, prepared above, in buffer at pH 6.8+0.3% SLS is shown in Table 20 (see also FIG. 7).

TABLE 20

| | APREMILAST Tablets | | | |
|---|---|---|---|---|
| | Sample 001 (Form B) | | Sample 004 (Form N) | |
| | Assay: 95.1% | | Assay: 93.7% | |
| Time | n = 3 | | | |
| [min] | Mean | RSD | Mean | RSD |
| 5 | 38.6 | 4.3 | 63.3 | 3.3 |
| 10 | 47.8 | 4.5 | 81.4 | 4.6 |
| 15 | 52.5 | 4.0 | 87.3 | 5.3 |
| 20 | 55.4 | 5.0 | 89.6 | 5.4 |
| 30 | 60.3 | 4.8 | 91.2 | 5.4 |
| 45 | 65.4 | 6.3 | 91.6 | 5.5 |
| 60 | 68.9 | 6.4 | 91.8 | 5.7 |

When compared with prior art Form B, Form N exhibits a higher dissolution rate by more than 50% at 30 minutes.

CITED LITERATURE

EP2276483 B1; U.S. Pat. No. 6,962,940

The invention claimed is:

1. Crystalline Form N of N-[2-[(1S)-1-(3-ethoxy-4-methoxyphenyl)-2-(methylsulfonyl) ethyl]-1,3-dioxo-2,3-dihydro-1H-isoindol-4-yl]acetamide), having an X-ray powder diffraction pattern with peaks at 2-theta angles of 9.9±0.2 degrees 2theta, 12.7±0.2 degrees 2theta, 18.8±0.2 degrees 2theta, 20.2±0.2 degrees 2theta, 22.1±0.2 degrees 2theta, 24.0±0.2 degrees 2theta, and 29.4±0.2 degrees 2theta when using Cu-Kα radiation.

2. The crystalline form of claim 1, wherein the X-ray powder diffraction pattern is free of further peaks having an intensity which is higher than the intensity of the peak at 18.8±0.2 degrees 2theta.

3. The crystalline form of claim 1, which
   (i) is unsolvated and has a solvent content of less than 1 wt.-%, wherein the solvent content is determined by gas chromatographic (GC) analysis; and/or
   (ii) has a mass loss of less than 0.5% of the total mass of a sample in a thermogravimetric analysis (TGA) upon heating from 25° C. to 220° C. with a gradient of 7° C./min.

4. The crystalline form of claim 1,
   (i) having a single endothermic event in a differential scanning calorimeter plot with an onset temperature of about 139° C.±6° C., about 139° C.±4° C., or about 139° C.±2° C.; and/or
   (ii) wherein the X-ray powder diffraction pattern has further peaks at 2-theta angles of 11.7±0.2 degrees 2theta, 11.9±0.2 degrees 2theta, 13.7±0.2 degrees 2theta, 14.4±0.2 degrees 2theta, 14.6±0.2 degrees 2theta, 15.3±0.2 degrees 2theta, 16.7±0.2 degrees 2theta, 21.4±0.2 degrees 2theta, 23.0±0.2 degrees 2theta, 23.7±0.2 degrees 2theta, 24.8±0.2 degrees 2theta, 25.6±0.2 degrees 2theta, 26.8±0.2 degrees 2theta, and 29.8±0.2 degrees 2theta, when using Cu-Kα radiation; and/or
   (iii) which contains less than 5 wt.-% of other crystalline, non-crystalline or amorphous forms of N-[2-[(1S)-1-(3-ethoxy-4-methoxyphenyl)-2-(methylsulfonyl) ethyl]-1,3-dioxo-2,3-dihydro-1H-isoindol-4-yl]acetamide.

5. The crystalline form of claim 4,
(i) having a single endothermic event in a differential scanning calorimeter plot with an onset temperature of about 139° C.±6° C., about 139° C.±4° C., or about 139° C.±2° C.

6. The crystalline form of claim 4,
(ii) wherein the X-ray powder diffraction pattern has further peaks at 2-theta angles of 11.7±0.2 degrees 2theta, 11.9±0.2 degrees 2theta, 13.7±0.2 degrees 2theta, 14.4±0.2 degrees 2theta, 14.6±0.2 degrees 2theta, 15.3±0.2 degrees 2theta, 16.7±0.2 degrees 2theta, 21.4±0.2 degrees 2theta, 23.0±0.2 degrees 2theta, 23.7±0.2 degrees 2theta, 24.8±0.2 degrees 2theta, 25.6±0.2 degrees 2theta, 26.8±0.2 degrees 2theta, and 29.8±0.2 degrees 2theta, when using Cu-Kα radiation.

7. The crystalline form of claim 4,
(iii) which contains less than 5 wt.-% of other crystalline, non-crystalline or amorphous forms of N-[2-[(1S)-1-(3-ethoxy-4-methoxyphenyl)-2-(methylsulfonyl)ethyl]-1,3-dioxo-2,3-dihydro-1H-isoindol-4-yl]acetamide.

8. A pharmaceutical composition or dosage form comprising a crystalline form of claim 4.

9. The crystalline form of claim 3, which
(i) is unsolvated and has a solvent content of less than 1 wt.-%, wherein the solvent content is determined by gas chromatographic (GC) analysis.

10. The crystalline form of claim 3, which
(ii) has a mass loss of less than 0.5% of the total mass of a sample in a thermogravimetric analysis (TGA) upon heating from 25° C. to 220° C. with a gradient of 7° C./min.

11. A pharmaceutical composition or dosage form comprising a crystalline form of claim 1.

12. The pharmaceutical composition or dosage form of claim 11, which comprises at least one pharmaceutically acceptable excipient and/or which is a tablet.

13. A process for preparing an oral solid pharmaceutical dosage form of claim 11, comprising a step of compressing (i) a mixture of Form N with one or more pharmaceutical acceptable excipients, or (ii) granules including Form N, optionally in admixture with one or more pharmaceutical acceptable excipients.

14. A method of treating a disease or disorder selected from the group consisting of: psoriasis; psoriatic arthritis; rheumatoid arthritis; chronic cutaneous sarcoid; giant cell arteritis; Parkinson's Disease; prurigo nodularis; lichen planus; complex apthosis; Behcet's Disease; lupus; hepatitis; uveitis; Sjogren's Disease; depression; interstitial cystitis; vulvodynia; prostatitis; osteoarthritis; diffuse large B cell lymphoma; polymyositis; dermatomyositis; inclusion body myositis; erosive osteoarthritis; hepatitis; endometriosis; radiculopathy; and pyoderma gangrenosum, comprising administering to a subject in need thereof an effective amount of a pharmaceutical composition or dosage form according to claim 8.

15. A method of treating a disease or disorder selected from the group consisting of: HIV; hepatitis; adult respiratory distress syndrome; bone resorption diseases; chronic obstructive pulmonary diseases; chronic pulmonary inflammatory diseases; dermatitis; inflammatory skin disease, atopic dermatitis, cystic fibrosis; septic shock; sepsis; endotoxic shock; hemodynamic shock; sepsis syndrome; post ischemic reperfusion injury; meningitis; psoriasis; psoriatic arthritis; fibrotic disease; cachexia; graft rejection; auto immune disease; rheumatoid spondylitis; arthritic conditions; osteoporosis; Crohn's disease; ulcerative colitis; inflammatory bowel disease; multiple sclerosis; systemic lupus erythrematosus; erythema nodosum leprosum in leprosy; radiation damage; asthma; and hyperoxic alveolar injury, comprising administering to a subject in need thereof an effective amount of a pharmaceutical composition or dosage form according to claim 8.

16. A method of treating a disease or disorder selected from the group consisting of: psoriasis; psoriatic arthritis; rheumatoid arthritis; chronic cutaneous sarcoid; giant cell arteritis; Parkinson's Disease; prurigo nodularis; lichen planus; complex apthosis; Behcet's Disease; lupus; hepatitis; uveitis; Sjogren's Disease; depression; interstitial cystitis; vulvodynia; prostatitis; osteoarthritis; diffuse large B cell lymphoma; polymyositis; dermatomyositis; inclusion body myositis; erosive osteoarthritis; hepatitis; endometriosis; radiculopathy; and pyoderma gangrenosum, comprising administering to a subject in need thereof an effective amount of a pharmaceutical composition or dosage form comprising a crystalline form of claim 3.

17. A method of treating a disease or disorder selected from the group consisting of: HIV; hepatitis; adult respiratory distress syndrome; bone resorption diseases; chronic obstructive pulmonary diseases; chronic pulmonary inflammatory diseases; dermatitis; inflammatory skin disease, atopic dermatitis, cystic fibrosis; septic shock; sepsis; endotoxic shock; hemodynamic shock; sepsis syndrome; post ischemic reperfusion injury; meningitis; psoriasis; psoriatic arthritis; fibrotic disease; cachexia; graft rejection; auto immune disease; rheumatoid spondylitis; arthritic conditions; osteoporosis; Crohn's disease; ulcerative colitis; inflammatory bowel disease; multiple sclerosis; systemic lupus erythrematosus; erythema nodosum leprosum in leprosy; radiation damage; asthma; and hyperoxic alveolar injury, comprising administering to a subject in need thereof an effective amount of a pharmaceutical composition or dosage form comprising a crystalline form of claim 3.

18. A method of treating a disease or disorder selected from the group consisting of: psoriasis; psoriatic arthritis; rheumatoid arthritis; chronic cutaneous sarcoid; giant cell arteritis; Parkinson's Disease; prurigo nodularis; lichen planus; complex apthosis; Behcet's Disease; lupus; hepatitis; uveitis; Sjogren's Disease; depression; interstitial cystitis; vulvodynia; prostatitis; osteoarthritis; diffuse large B cell lymphoma; polymyositis; dermatomyositis; inclusion body myositis; erosive osteoarthritis; hepatitis; endometriosis; radiculopathy; and pyoderma gangrenosum, comprising administering to a subject in need thereof an effective amount of a pharmaceutical composition or dosage form according to claim 11.

19. A method of treating a disease or disorder selected from the group consisting of: HIV; hepatitis; adult respiratory distress syndrome; bone resorption diseases; chronic obstructive pulmonary diseases; chronic pulmonary inflammatory diseases; dermatitis; inflammatory skin disease, atopic dermatitis, cystic fibrosis; septic shock; sepsis; endotoxic shock; hemodynamic shock; sepsis syndrome; post ischemic reperfusion injury; meningitis; psoriasis; psoriatic arthritis; fibrotic disease; cachexia; graft rejection; auto immune disease; rheumatoid spondylitis; arthritic conditions; osteoporosis; Crohn's disease; ulcerative colitis; inflammatory bowel disease; multiple sclerosis; systemic lupus erythrematosus; erythema nodosum leprosum in leprosy; radiation damage; asthma; and hyperoxic alveolar injury, comprising administering to a subject in need thereof an effective amount of a pharmaceutical composition or dosage form according to claim 11.

20. A method of treating graft versus host disease, rheumatoid arthritis or osteoarthritis, comprising administering to a subject in need thereof an effective amount of a pharmaceutical composition or dosage form according to claim 11.

* * * * *